(12) United States Patent
Hartle et al.

(10) Patent No.: US 8,893,429 B2
(45) Date of Patent: Nov. 25, 2014

(54) MANUFACTURED SEED HAVING A TREATED END SEAL ASSEMBLY

(75) Inventors: Jeffrey E. Hartle, Bonney Lake, WA (US); William C. Carlson, Olympia, WA (US); Craig N. Cootsona, Tacoma, WA (US); Russell T. Barham, Seattle, WA (US); Katie A. Brinkerhoff, Puyallup, WA (US); Jessica M. King, Lakewood, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 307 days.

(21) Appl. No.: 13/533,213

(22) Filed: Jun. 26, 2012

(65) Prior Publication Data

US 2013/0007921 A1    Jan. 3, 2013

Related U.S. Application Data

(60) Provisional application No. 61/502,754, filed on Jun. 29, 2011.

(51) Int. Cl.
*A01C 1/06* (2006.01)
*A01C 21/00* (2006.01)
*A01H 4/00* (2006.01)

(52) U.S. Cl.
CPC ........................... *A01H 4/006* (2013.01)
USPC .................................................. 47/57.6

(58) Field of Classification Search
USPC ............... 47/57.6, DIG. 9; 800/200; 435/420
See application file for complete search history.

(56) References Cited

U.S. PATENT DOCUMENTS

| | | | |
|---|---|---|---|
| 5,701,699 A | 12/1997 | Carlson et al. | |
| 6,119,395 A | 9/2000 | Hartle et al. | |
| 6,931,787 B2 | 8/2005 | Hirahara et al. | |
| 7,131,234 B2 | 11/2006 | Carlson et al. | |
| 7,168,205 B2 * | 1/2007 | Hartle et al. | 47/57.6 |
| 7,795,377 B2 | 9/2010 | Carlson et al. | |

* cited by examiner

*Primary Examiner* — Kent L Bell
(74) *Attorney, Agent, or Firm* — Baker Hostetler LLP

(57) ABSTRACT

The present disclosure includes a manufactured seed comprising a seed shell and a restraint disposed within the seed shell. The seed shell is a structure having an open end and a closed end. A primary end seal is disposed on the open end of the seed shell. A secondary end seal is arranged on the primary end seal, the secondary end seal being coated, at least partially, with a paraffin oil.

16 Claims, 24 Drawing Sheets

MANUFACTURED SEED HAVING A TREATED END SEAL ASSEMBLY

CROSS-REFERENCE TO RELATED APPLICATIONS

This application is entitled to and claims the benefit of priority under 35 U.S.C. §119 from U.S. Provisional Patent Application Ser. No. 61/502,754 filed Jun. 29, 2011, and titled "Manufactured Seed Having Treated End Seal Assembly," the contents of which are incorporated herein by reference.

This application relates to the following applications, filed on the same day as the present patent application, the contents of which are all incorporated herein by reference:

U.S. patent application Ser. No. 13/533,246 and titled "Manufactured Seed Having Parabolic Cavity;"

U.S. patent application Ser. No. 13/533,260 and titled "Manufactured Seed Having Parabolic Cavity;" and U.S. patent application Ser. No. 13/533,486 and titled "Manufactured Seed Having Parabolic End Seal Assembly;"

U.S. patent application Ser. No. 13/533,287, and titled "Manufactured Seed Having Parabolic End Seal Assembly and Parabolic Cavity;" and U.S. patent application Ser. No. 13/533,540 and titled "Manufactured Seed Having Embryo Disposed Therein."

TECHNICAL FIELD

The present disclosure is directed generally to improved designs for manufactured seeds and manufactured seed components.

BACKGROUND

Modern research leading to the successful demonstration of encapsulation of tissue culture derived from plants has initiated a line of research focused on the development of synthetic or "manufactured" seeds. Manufactured seeds generally include encapsulated somatic or zygotic plant embryos that functionally mimic development of naturally propagated seeds. Such manufactured seeds may reduce labor costs and increase efficiency in many modern agriculture (including silviculture) applications. Examples of manufactured seeds are disclosed, for example, in U.S. Pat. No. 5,701,699, issued to Carlson et al., the disclosure of which is hereby expressly incorporated by reference.

Typical manufactured seeds include a seed shell, synthetic gametophyte, and a plant embryo. A manufactured seed that does not include the plant embryo is known in the art as a "seed blank." The seed blank typically is a cylindrical capsule having a closed end and an open end. The synthetic gametophyte is placed within the seed shell to substantially fill the interior of the seed shell. A longitudinally extending hard porous insert, known as a shoot restraint, may be centrally located within one end of the seed shell, surrounded by the synthetic gametophyte, and includes a centrally located cavity extending partially through the length of the shoot restraint. The plant embryo is deposited within the cavity of the shoot restraint. The plant embryo is then sealed within the seed blank by an end seal, which may be coated with an antibiotic substance.

Although known manufactured seeds are generally effective in providing an inexpensive delivery unit for plant tissue culture, there are many opportunities to improve current seed design. For example, one problem with some manufactured seeds involves low numbers of successful germinants. Many factors can lead to germination failure; however, most manufactured seeds typically exhibit some form of abnormal growth that indicates germination may not be successful. Being able to identify abnormal growth patterns and provide seed design solutions could significantly help advance manufactured seed technology.

Thus, there is a need to continually improve the design of manufactured seeds to reduce abnormal growth of embryos. Improvements to manufactured seed design that lead to an increased number of successful and vigorous germinants (when compared with conventional manufactured seed designs) would be particularly desirable in this field of developing technology. Ideally, seed design improvements may also help improve cost and efficiency models for utilization of manufactured seed technology.

SUMMARY

The following summary is provided for the benefit of the reader only and is not intended to limit in any way the invention as set forth by the claims. The present disclosure is directed generally towards improved designs for manufactured seeds and manufactured seed components.

The present disclosure includes a manufactured seed comprising a seed shell and a restraint disposed within the seed shell. The seed shell is a structure having an open end and a closed end. A primary end seal is disposed on the open end of the seed shell. A secondary end seal is arranged on the primary end seal, the secondary end seal being coated, at least partially, with a paraffin oil.

BRIEF DESCRIPTION OF THE DRAWINGS

The present disclosure is better understood by reading the following description of non-limitative embodiments with reference to the attached drawings wherein like parts of each of the figures are identified by the same reference characters, and are briefly described as follows.

DETAILED DESCRIPTION

Figure 1:
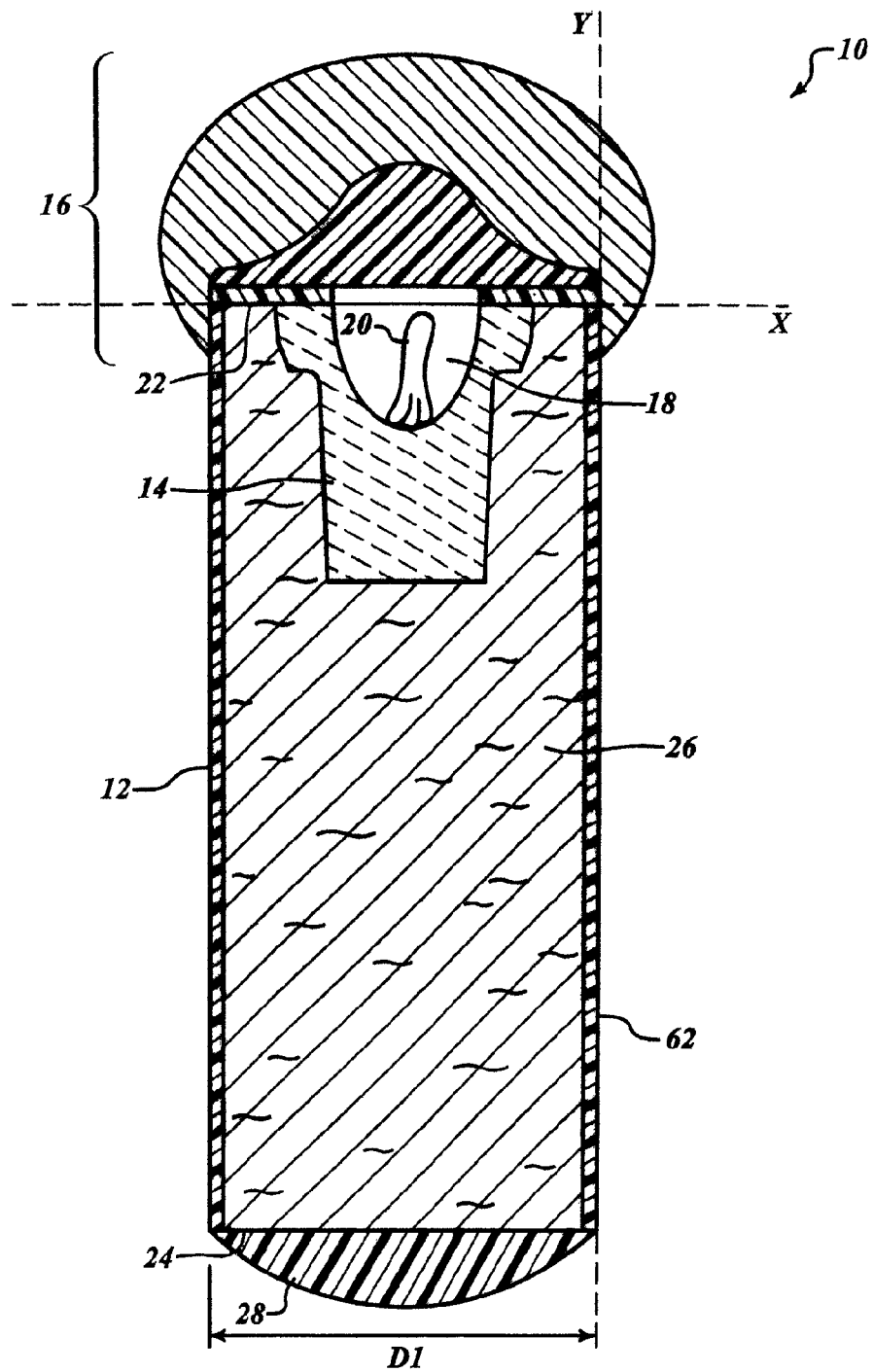
FIG. 1 is a side cross-sectional view of an embodiment of a manufactured seed according to the disclosure.

The present disclosure describes improved designs for manufactured seeds and manufactured seed components. Certain specific details are set forth in the following description and FIGS. 1-35 to provide a thorough understanding of various embodiments of the disclosure. Well-known structures, systems, and methods often associated with such systems have not been shown or described in detail to avoid unnecessarily obscuring the description of various embodiments of the disclosure. In addition, those of ordinary skill in the relevant art will understand that additional embodiments of the disclosure may be practiced without several of the details described below. Certain terminology used in the disclosure are defined as follows:

"Agricultural crop" refers to cultivated plants or agricultural produce such as grain, vegetables, or fruit. As non-limiting examples, agricultural crops according to the disclosure include corn, soybean, rice, wheat, sugar cane, canola, coffee, banana, and cotton.

"Cotyledon" refers generally to the first, first pair, or first whorl (depending on the plant type) of leaf-like structures on the plant embryo that function primarily to make food compounds in the seed available to the developing embryo but in some cases act as food storage or photosynthetic structures.

"Dead end" refers to the closed end of a manufactured seed.

"Dimple" refers to depressions, indentations, or protrusions in a surface of a material. Examples of various types of dimples according to embodiments of the disclosure are illustrated in the Figures.

"Epicotyl" refers to the portion of the plant developed after germination from the stem apex.

"Functional contact" with respect to orientation of embryos according to the disclosure is intended to mean in a position in which the embryo is configured to uptake nutrients from the nutritive media.

"Germinant" means an embryo that has undergone sufficient growth and developments to protrude from the seed shell of a manufactured seed. This stage is generally analogous to protruding from a natural botanic seed.

"Hypertrophy" refers to a type of abnormal growth characterized by abnormally large or swollen portions of the embryo.

"Hypocotyl" refers to the portion of the plant embryo or seedling located below the cotyledons but above the radicle.

"Live end" refers to the open end of a manufactured seed.

"Nutritive media" refers to a source of nutrients, such as vitamins, minerals, carbon, and energy sources, and other beneficial compounds used by the embryo during germination.

"Parabolic" refers to a geometric configuration having at least one parabolic cross-sectional area and at least one elliptical and/or circular cross-sectional area. Examples of parabolic configurations according to embodiments of the disclosure are illustrated in the Figures.

"Paraffin oil" refers to mineral oil or any other type of oil having heavier alkanes (a density of approximately around 0.8 $g/cm^3$) including, but not limited to nujol, adepsine oil, alboline, glymol, medicinal paraffin, or saxol.

"Radicle" refers to the part of a plant embryo that develops into the primary root of the resulting plant.

"Root end" or "root portion" with respect to a plant embryo refers to the portion of the embryo from which the non-aerial part of the plant originates.

"Shoot end" or "shoot portion" with respect to a plant embryo refers to the portion of the embryo from which the aerial part of the plant originates.

"Somatic embryo" is a plant embryo that developed via laboratory culturing of totipotent plant cells or by induced cleavage polyembryony.

"Tree" refers to any type of woody perennial plant. The disclosure is not intended to be limited to a particular species or type of tree.

"Zygotic embryo" refers to a plant embryo originating from a natural seed of the corresponding plant.

Overview

Referring to FIGS. 1, 2, 6, 7, 16-21 a manufactured seed 10 constructed in accordance with embodiments of the disclosure is shown arranged on a coordinate system comprising an x-axis (X), a y-axis (Y), and a z-axis (Z). FIGS. 3-5, 8-15, 22-26 depict details of embodiments of various components of the manufactured seeds 10. FIGS. 1, 6, 16, 18, and 20 generally illustrate embodiments of manufactured seeds that are particularly useful in applications involving tree embryos. FIGS. 2, 7, 17, 19, and 21 generally illustrate embodiments of manufactured seeds that are particularly useful in applications involving embryos from agricultural crops. However, a person of ordinary skill in the art will appreciate that manufactured seeds having a structure or design that is substantially similar to those shown in FIGS. 1, 6, 16, 18, and 20 may be used with agricultural crop embryos. Similarly, manufactured seeds having a structure or design that is substantially similar to those shown in FIGS. 2, 7, 17, 19, and 21 may be used with tree embryos.

Figure 2:
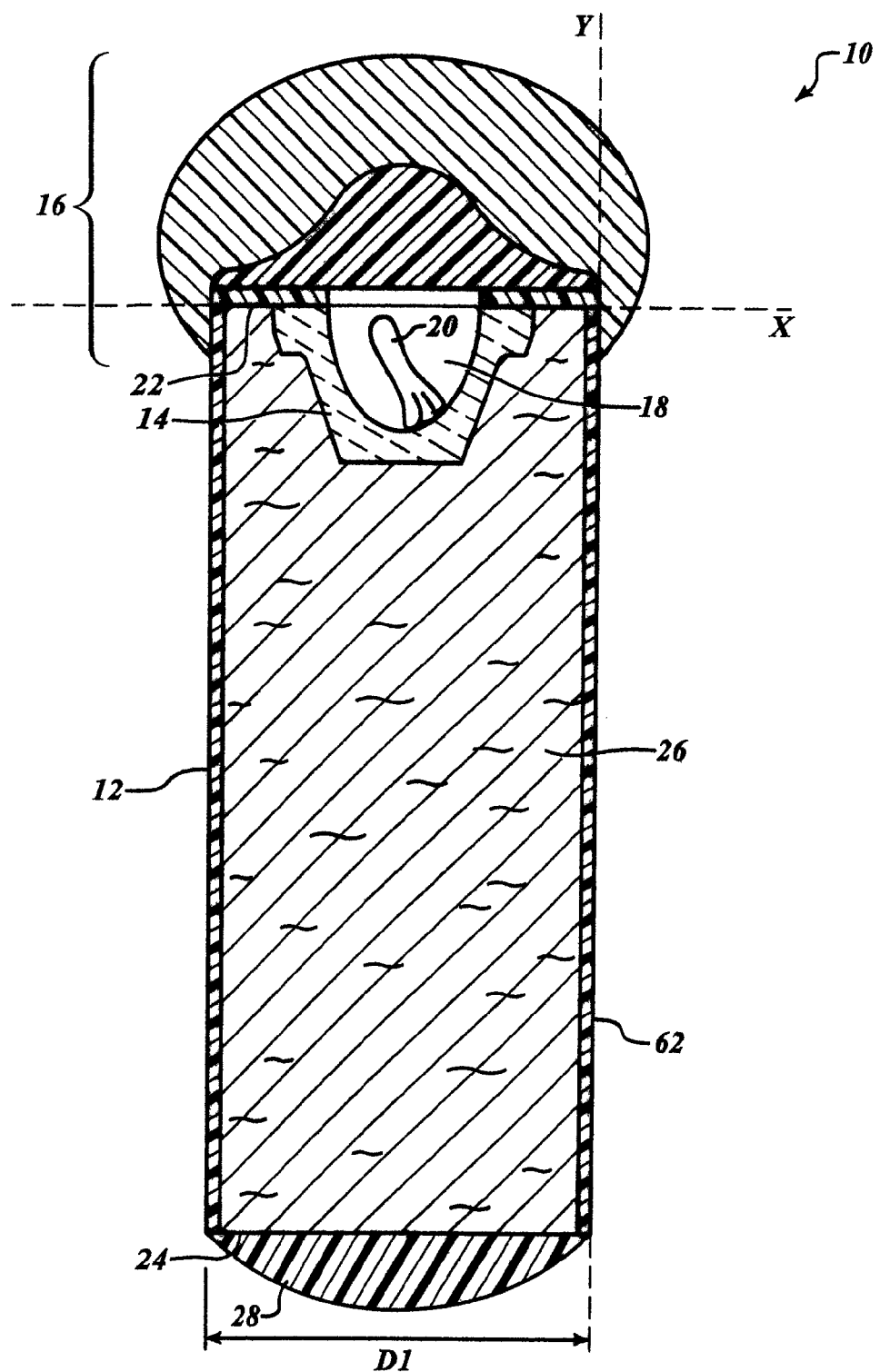
FIG. 2 is a side cross-sectional view of another embodiment of a manufactured seed according to the disclosure.

Referring to FIGS. 1 and 2, manufactured seeds 10 according to embodiments of the disclosure generally include the following components: a seed shell 12, a shoot restraint 14 disposed within the seed shell 12, and a seal assembly 16 (e.g., a live end seal). The shoot restraint 14 includes a longitudinally extending cavity 18 that extends at least partially through the length of the shoot restraint 14. An embryo 20 may be disposed in the cavity 18.

Manufactured seeds according to embodiments of the disclosure include seed design features intended to promote healthy and vigorous germination. Seed design features according to embodiments of the disclosure are based on identifying and inhibiting abnormal growth. For example, some studies have shown that one type of abnormal growth—hypertrophy—can limit axial elongation of the embryo, thereby resulting in failure to shed the seed shell. Thus, manufactured seeds according to embodiments of the disclosure have been modified to reduce the mechanical resistance (e.g., including but not limited to hypertrophy) that can cause abnormal growth patterns or inhibit germination for embryos that may already exhibit abnormal growth patterns.

There are many other examples of abnormal growth patterns that may indicate a higher potential for germination failure. Some studies show that during development, embryos may become stuck on the seal assembly and/or open end of the seed shell while exiting the manufactured seed. In other situations, germination may be inhibited because the breaking strength of the seal assemblies are too weak or too strong. If the breaking strength is too strong, the seal assemblies do not break and allow the growing embryo to emerge from the seed shell. On the other hand, if the end seals are too weak, seal assemblies can rupture prematurely before the embryo is sufficiently developed, thereby inhibiting germination. In addition, some evidence suggests that conventional coatings for end seals (e.g. triple antibiotic ointment) are possibly detrimental to germination. Features of manufactured seeds 10 according to embodiments of the disclosure, including features of their various components, are described in further detail below.

Seed Shell

Figure 3:
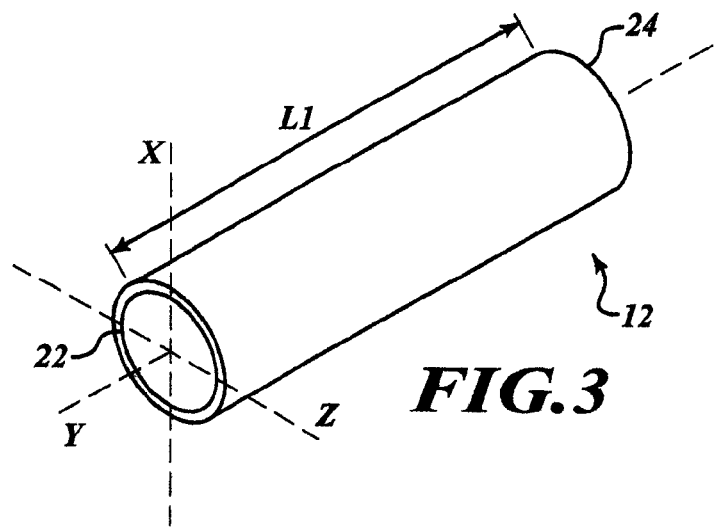
FIG. 3 is a perspective view of a seed shell according to embodiments of the disclosure.
Figure 4:
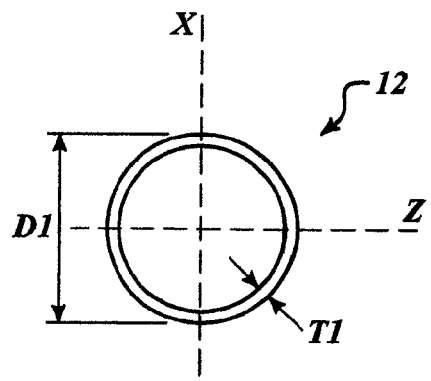
FIG. 4 is a top plan view of the seed shell from FIG. 3.
Figure 5:
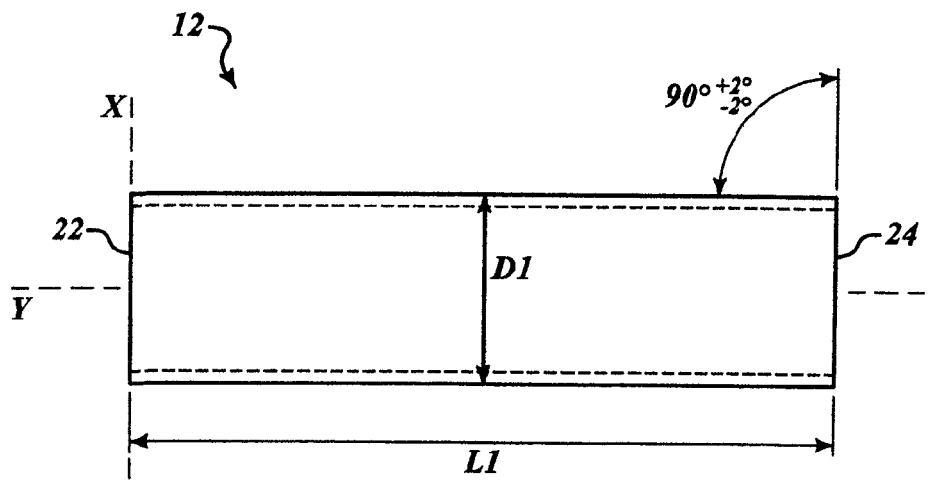
FIG. 5 is a side cross-sectional view of the seed shell from FIGS. 3 and 4.

FIGS. 3-5 illustrate details of seed shells 12 according to embodiments of the disclosure. In some embodiments, the seed shell 12 may be suitably formed from a section of tubular material. In other embodiments, the seed shell may spherical, ovaloid, cubical, or any other shape that would be suitable to a person of ordinary skill in the art. As shown In FIGS. 1-3 and 5, the seed shell 12 has an open end 22 (e.g., a live end) and a closed end 24 (e.g., a dead end seal). As shown in FIGS. 1 and 2, the closed end 24 may be sealed using an end seal 28 or any other means known to a person of ordinary skill in the art.

Seed shells 12 according to embodiments of the disclosure may be fabricated from a variety of materials including, but not limited to, cellulosic materials, glass, plastic, moldable plastic, cured polymeric resins, paraffin, waxes, varnishes, and combinations thereof such as a wax-impregnated paper. The materials from which the seed shell 12 is made are generally non-toxic and provide a degree of rigidity. The seed shell 12 can be biodegradable, although typically the seed shell remains intact and resistant to degradation until after emergence of the germinating embryo.

Referring to FIGS. 1 and 2, the seed shell 12 may be configured to house a nutritive medium 26 that is in functional contact with the embryo 20. Nutritive media 26 according to the disclosure may include a substance that causes the media to be a semi-solid or have a congealed consistency under normal environmental conditions. Suitable nutritive media 26 are described, for example, in U.S. Pat. No. 5,701,699 and U.S. Patent Application Ser. No. 61/387,244, the disclosures of which are hereby incorporated by reference.

As shown in FIGS. 3-5, seed shells 12 according to embodiments of the disclosure may have numerous different dimensions for use with different types of embryos. In some embodiments, the seed shell 12 has a seed shell diameter D1 ranging about 0.20 inches to about 0.30 inches. In other embodiments the seed shell diameter D1 may be about 0.30 inches to about 0.40 inches. The seed shell 12 also has a seed shell length L1 and a seed shell thickness T1. L1 may be approximately 0.75 inches to approximately 1.25 inches. T1 may be approximately 0.015 inches to approximately 0.030 inches.

Shoot Restraint

As described above, manufactured seeds 10 according to embodiments of the disclosure include a shoot restraint 14 disposed longitudinally within the seed shell 12. In some embodiments, the shoot portion of the embryo includes cotyledons. Sometimes the cotyledons may be removed from the shoot portion of the embryo prior to being disposed in the shoot restraint 14. In some cases, the shoot portion of the embryo does not have cotyledons. The shoot restraint 14 generally functions to discourage abnormal growth by preventing the shoot portion of the embryo from becoming trapped. FIGS. 6-15 illustrate details of shoot restraints 14 according to embodiments of the disclosure.

Figure 6:
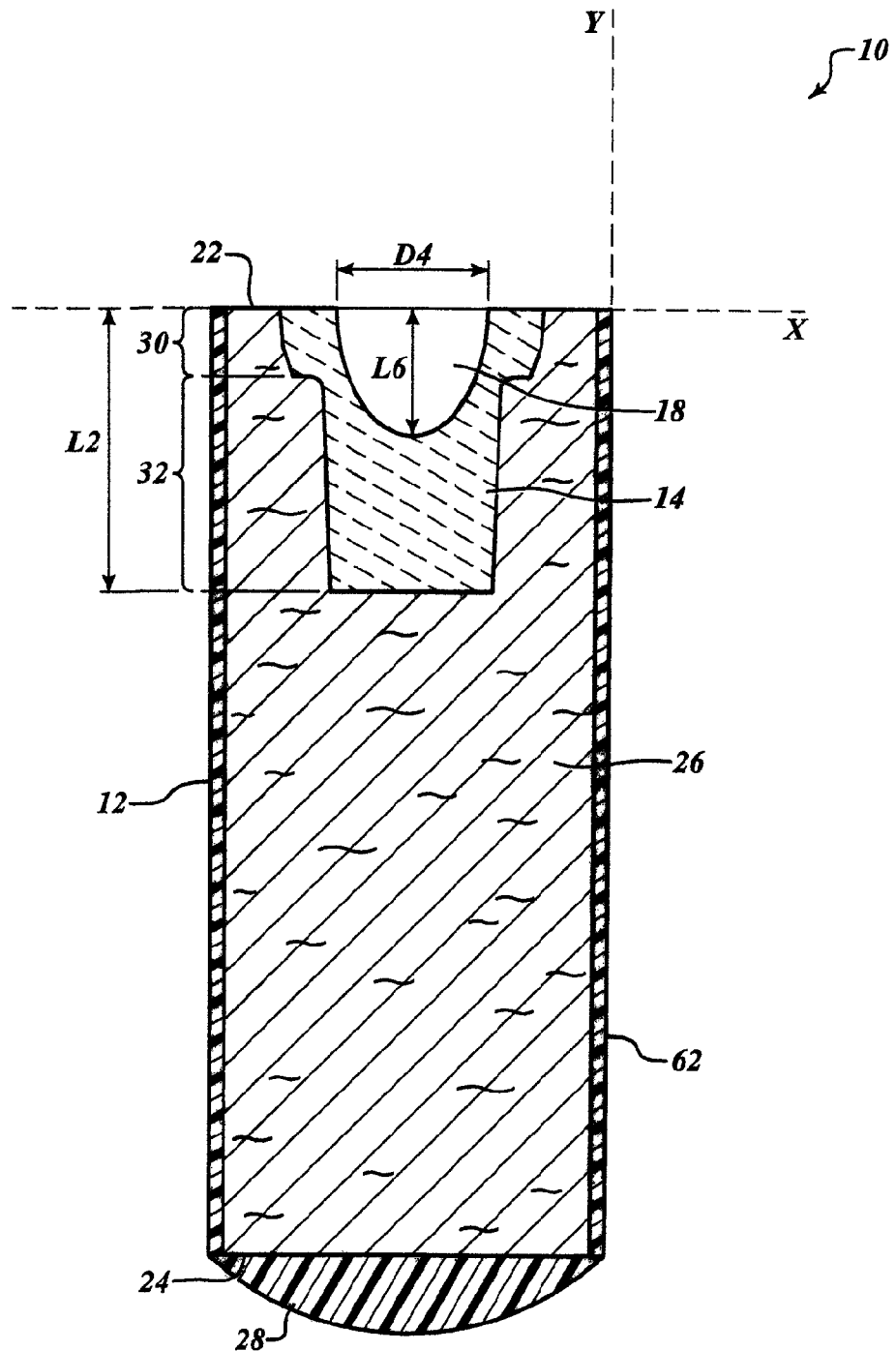
FIG. 6 is a side cross-sectional view of another embodiment of a manufactured seed according to the disclosure.
Figure 7:
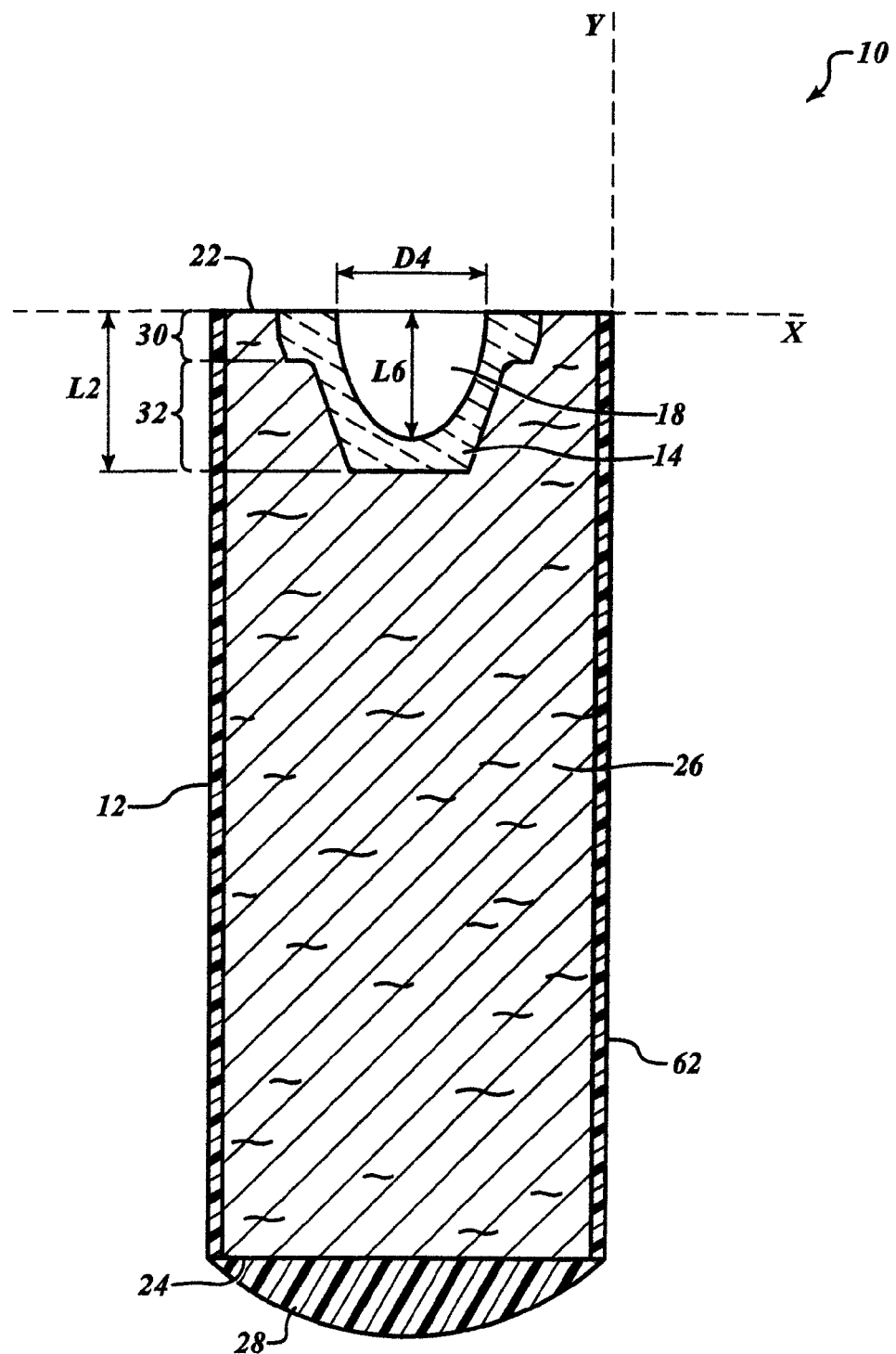
FIG. 7 is a side cross-sectional view of another embodiment of a manufactured seed according to the disclosure.
Figure 8:
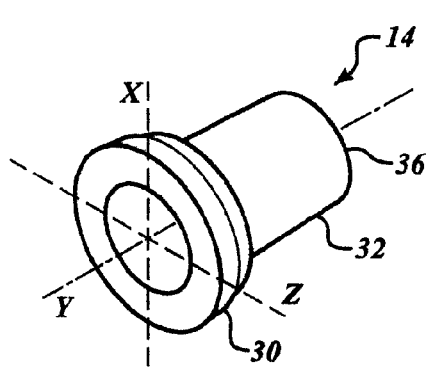
FIGS. 8 and 9 are perspective views of an embodiment of a restraint according to the disclosure.
Figure 9:
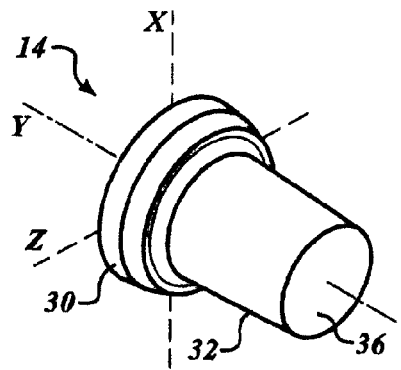
Figure 10:
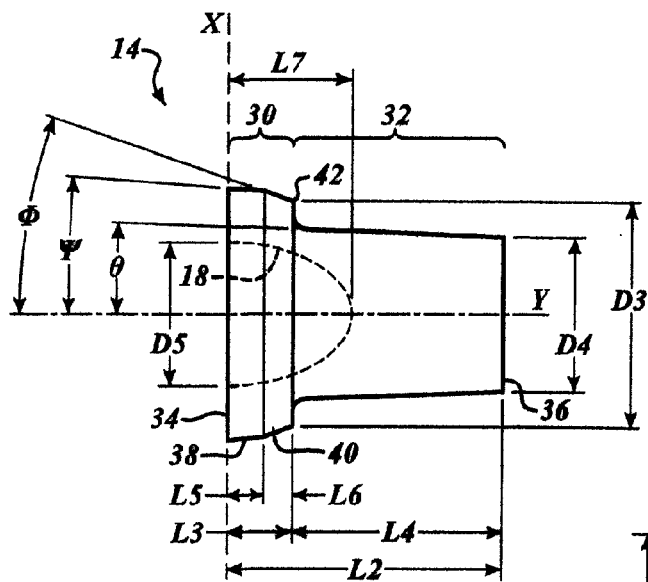
FIG. 10 is a side cross-sectional view of the restraint from FIGS. 8 and 9.

FIGS. 6 and 7 are side cross-sectional views of manufactured seeds according to embodiments of the disclosure without seal assemblies or embryos shown to better illustrate embodiments of suitable shoot restraints. In some embodiments, the shoot restraint 14 is centered to extend longitudinally into the seed shell 12. Shoot restraints 14 may be manufactured from a porous material having a hardness strong enough to resist puncture or fracture by a germinating embryo. Suitable materials include ceramic, porcelain, or other similar materials known to a person of ordinary skill in the art. The shoot restraint 14 generally includes a longitudinally extending cavity 18 that is configured to receive an embryo.

Shoot restraints 14 according to embodiments of the disclosure are configured to promote normal germination of embryos by providing a shape that facilitates healthy emergence of the embryos from the manufactured seed. Further, cavities 18 in the shoot restraints 14 according to embodiments of the disclosure have been designed to facilitate alternate orientations of embryos and to promote healthy germination analogous to that of a natural botanical seed. Specifically, cavities according to embodiments have a substantially parabolic shape that is expected to help promote germination by reducing the likelihood of abnormal growth.

FIGS. 8-15 illustrate further details of embodiments of shoot restraints 14 and cavities 18 according to the disclosure. In some embodiments, shoot restraints 14 include a substantially cylindrical upper portion 30, a substantially cylindrical lower portion 32, a top surface 34, a bottom surface 36, and a restraint depth L2. The top surface 34 and the bottom surface 36 have a substantially circular cross-section. A cavity 18 having a substantially parabolic shape extends from the top surface 34 to the bottom surface 36 through the upper portion 30 and at least partially into the lower portion 32. In some embodiments, the bottom surface 36 is chamfered. In other embodiments, the bottom surface 36 may be flat or rounded.

FIGS. 8-11 depict embodiments of shoot restraints 14 according to the disclosure similar to the restraint shown in FIG. 6. FIGS. 12-15 depict embodiments of shoot restraints 14 according to embodiments of the disclosure similar to the restraint shown in FIG. 7. Generally, FIGS. 8-11 depict a narrower and deeper shoot restraint 14 when compared to the restraints shown in FIGS. 12-15. Table 1 below summarizes suitable ranges for dimensions of the various components in restraints according to embodiments of the disclosure. Further, a person of ordinary skill in the art will appreciate that the restraints shown may be modified to include slightly different dimensions and configurations without departing from the spirit of the disclosure.

TABLE 1

Exemplary Dimensions for Restraints in FIGS. 8-15

| Dimension | Value in FIGS. 8-11 | Range for FIGS. 8-11 | Value in FIGS. 12-15 | Range for FIGS. 12-15 |
|---|---|---|---|---|
| L2 | 0.261 inches | 0.20 to 0.30 inches | 0.200 inches | 0.15 to 0.30 inches |
| L3 | 0.063 inches | 0.20 to 0.30 inches | 0.063 inches | 0.15 to 0.30 inches |
| L4 | 0.198 inches | 0.10 to .0250 inches | 0.137 inches | 0.10 to 0.15 inches |
| L5 | 0.035 inches | 0.01 to 0.05 inches | 0.035 inches | 0.01 to .05 inches |
| L6 | 0.028 inches | .001 to .05 inches | 0.028 inches | 0.01 to 0.05 inches |
| L7 | 0.118 inches | 0.09 to 0.220 inches | 0.118 inches | 0.09 to 0.220 inches |
| D2 | 0.240 inches | 0.15 to 0.30 inches | 0.325 inches | 0.20 to 0.35 inches |
| D3 | 0.214 inches | 0.15 to 0.29 inches | 0.299 inches | 0.25 to 0.35 inches |
| D4 | 0.147 inches | 0.10 to 0.18 inches | 0.140 inches | 0.10 to 0.16 inches |
| D5 | 0.144 inches | 0.10 to 0.20 inches | 0.234 inches | 0.10 to 0.30 inches |
| $\theta$ | 2 degrees | 0 to 5 degrees | 2 degrees | 0 to 5 degrees |
| $\Psi$ | 5 degrees | 0 to 7 degrees | 5 degrees | 0 to 7 degrees |
| $\Phi$ | 20 degrees | 0 to 25 degrees | 20 degrees | 0 to 25 degrees |

Figure 11:
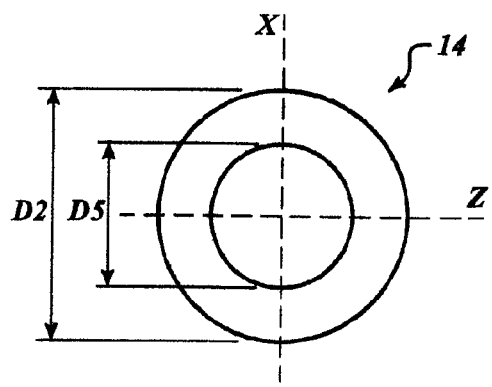
FIG. 11 is a top plan view of the restraint from FIGS. 8-10.
Figure 12:
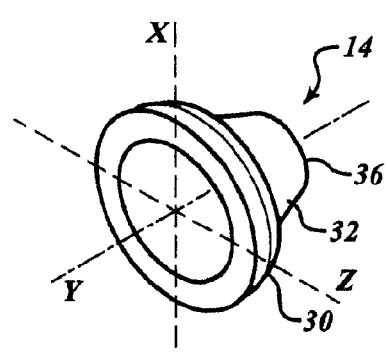
FIGS. 12 and 13 are perspective views of another embodiment of a restraint according to the disclosure.
Figure 13:
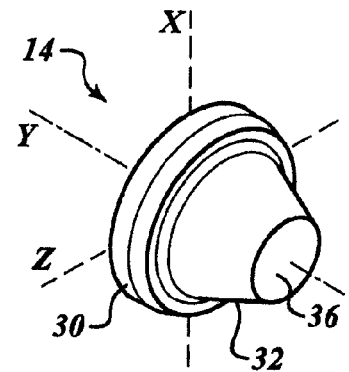
Figure 14:
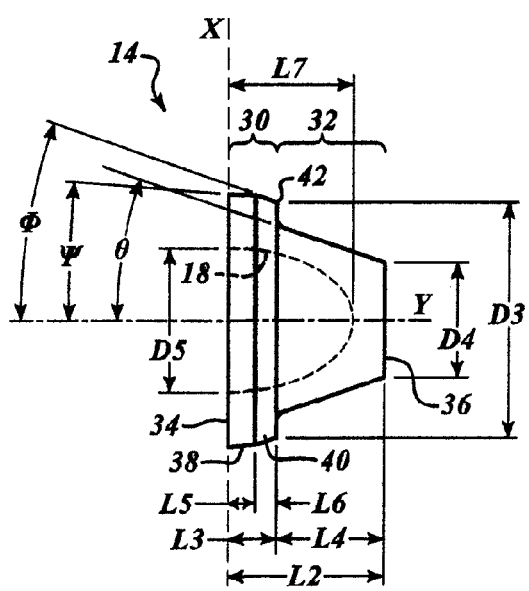
FIG. 14 is a side cross-sectional view of the restraint from FIGS. 12 and 13.
Figure 15:
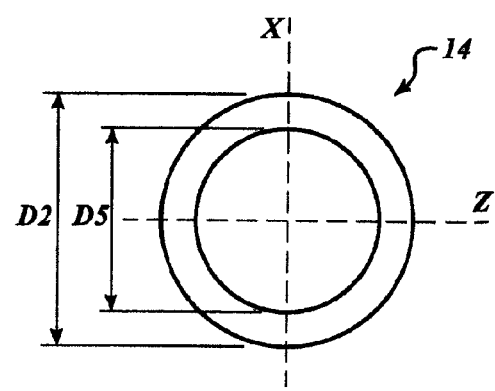
FIG. 15 is a top plan view of the restraint from FIGS. 12-14.
Figure 16:
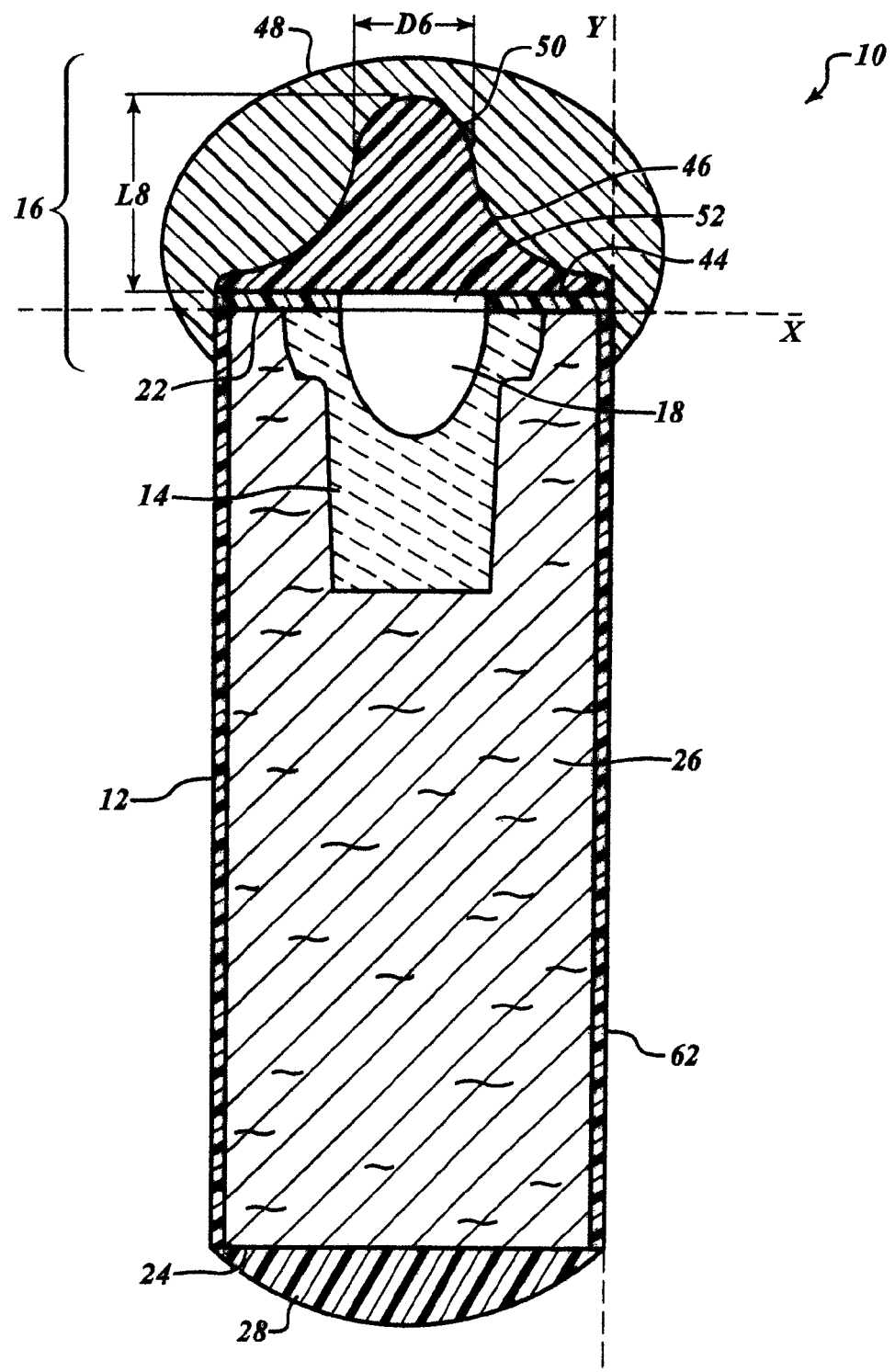
FIGS. 16-21 are side cross-sectional views of embodiments of a manufactured seed according to the disclosure.
Figure 17:
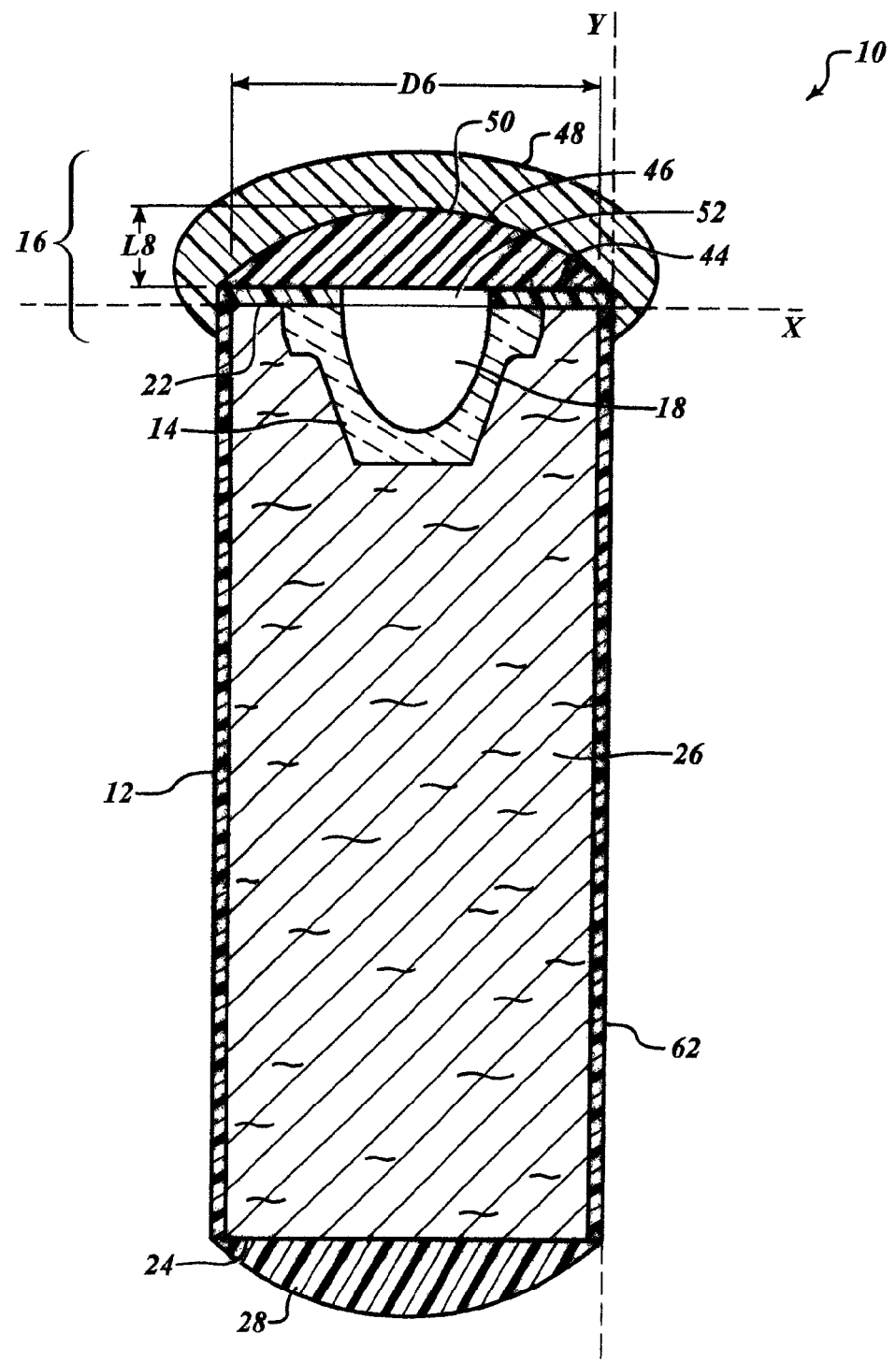
Figure 18:
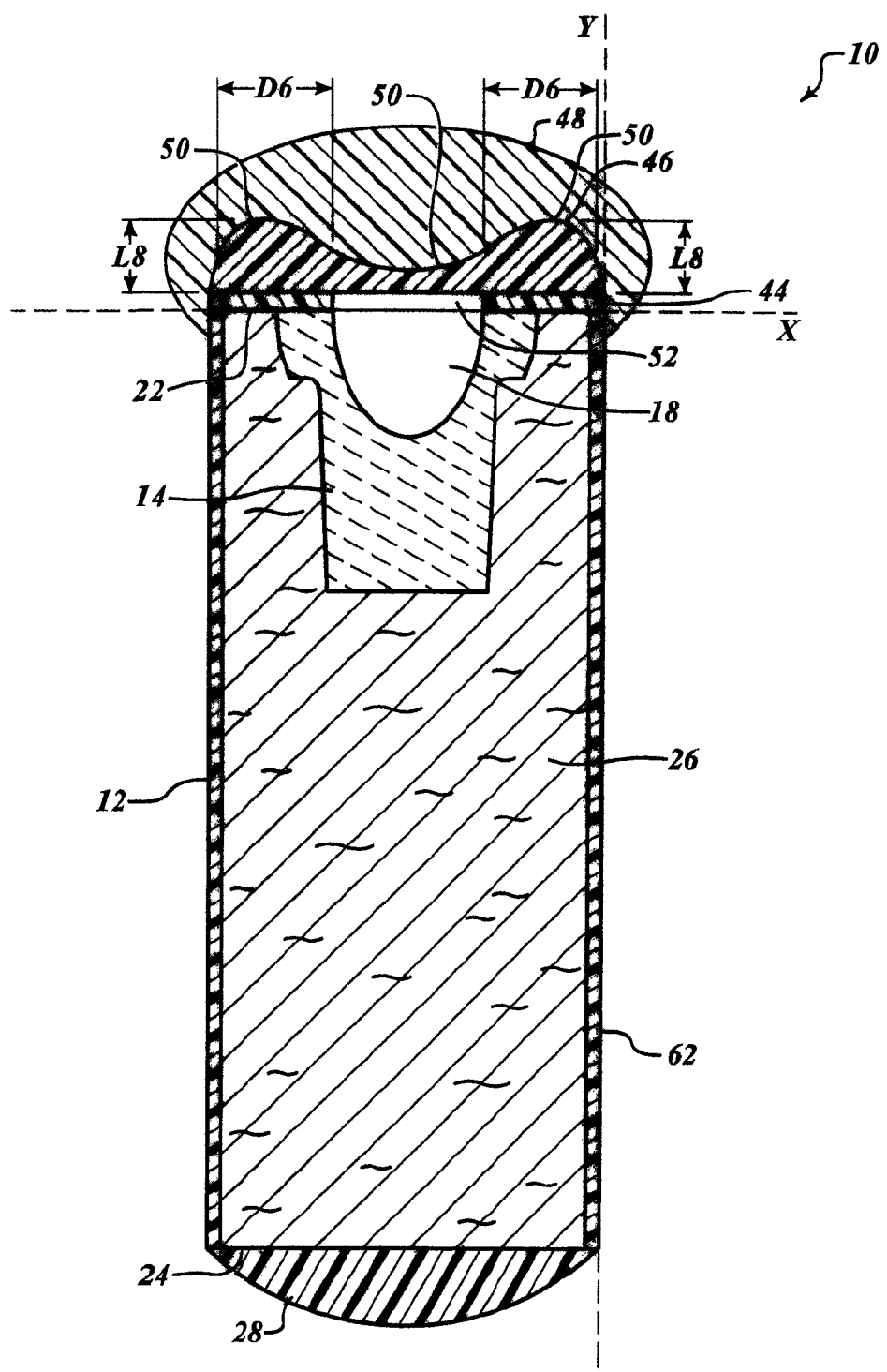
Figure 19:
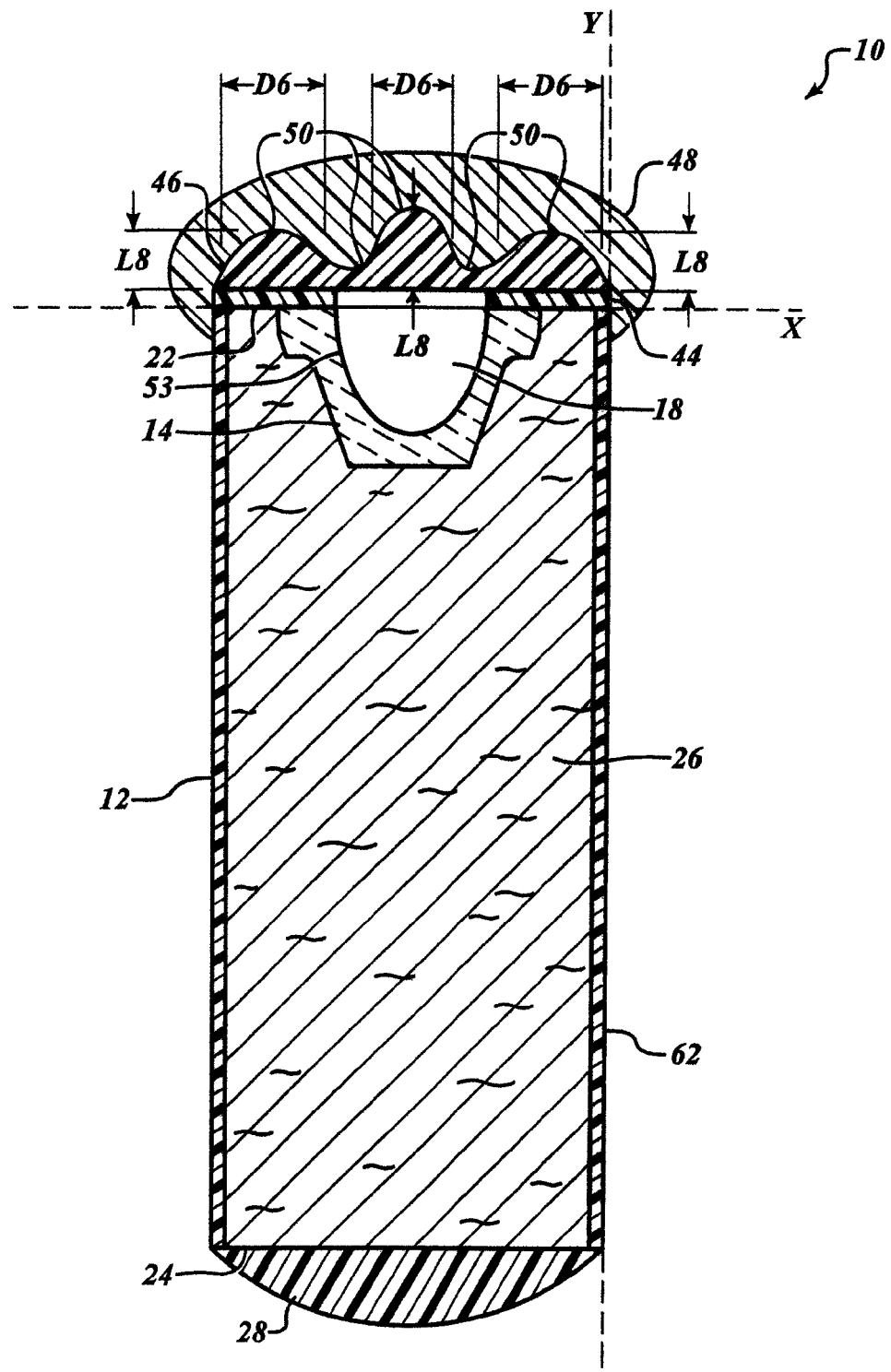
Figure 20:
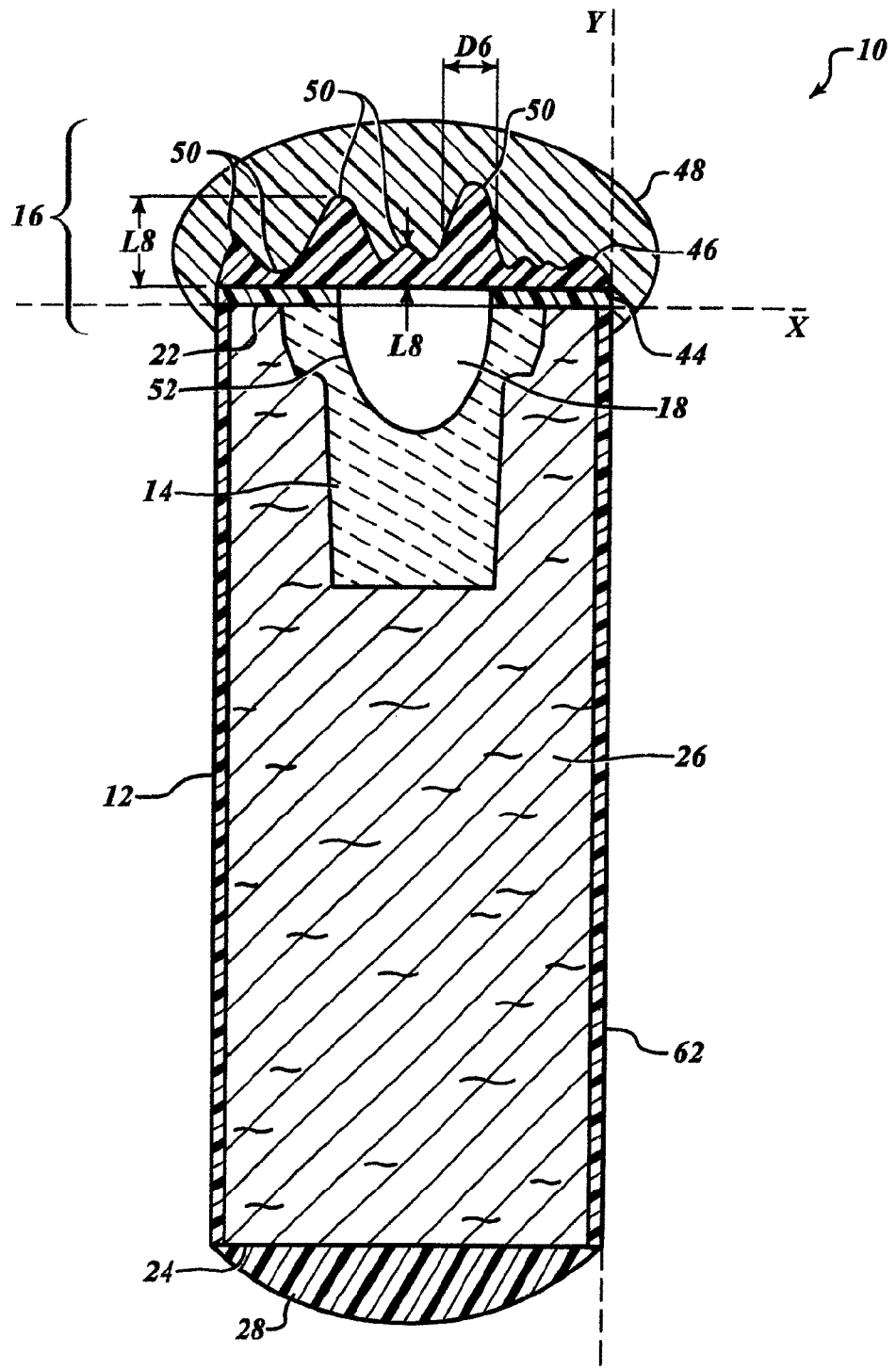

Referring to FIGS. 8-15, the upper portion 30 has an upper depth L3 and the lower portion 32 has a lower depth L4, the lower depth L4 being larger than the upper depth L3. In some embodiments, the upper portion 30 of the shoot restraint 14 may have a single diameter. Referring to FIGS. 11 and 15, the upper portion 30 may comprise an upper portion diameter D2. In other embodiments, the upper portion 30 of the shoot restraint 14 comprises one or more sections having varying diameters. For example, referring to FIGS. 10 and 14, the upper portion 30 may comprise a first section 38 (having a first section depth L5) and a second section 40 (having a second section depth L6). In some embodiments, the sidewalls of the first section 38 and the second section 40 are chamfered or angled with respect to the Y axis as depicted in the Figures. In other embodiments, the sidewalls of the upper portion 30 are substantially straight. In some embodiments, the upper portion 30 comprises an edge 42 having an edge diameter D3.

The lower portion 32 of the shoot restraint 14 may have sidewalls that are substantially straight with respect to the Y-axis or sidewalls that are substantially angled as shown in the Figures. In some embodiments, the sidewalls are tapered such that the lower portion 32 has a lower portion diameter D4 than is substantially smaller than the upper portion diameter D2.

Referring to FIGS. 8-15, the cavity 18 extending from the top surface 34 to the bottom surface 36 has a substantially parabolic shape and a cavity diameter D5 that varies along the length of the cavity 18. At its widest point, D5 may be about the same size as the upper portion diameter D2. In other embodiments, D5 may be slightly larger or smaller than the specific values disclosed provided that D5 does not exceed D2. Cavities 18 according to embodiments of the disclosure extend past the upper portion 30 and at least partially into the lower portion 32 as shown by a cavity depth L7.

Seal Assembly

As described above, manufactured seeds 10 according to embodiments of the disclosure include a seal assembly 16 disposed on the seed shell 12 to effectively seal the seed shell. FIGS. 16-23 depict various embodiments of seal assemblies 16 according to the disclosure. Referring to FIGS. 16-21, the seal assembly 16 includes a primary end seal 44 arranged on the open end 22 of the seed shell 12. The primary end seal 44 may suitably formed from biodegradable plastic and includes a centrally located opening 52. The opening 52 is sized to correspond to the diameter of the cavity 18 (D5) to permit a germinating embryo (not shown in this Figure) to pass through. The primary end seal 44 may be suitably attached by a variety of well-known methods, including glue or heat bonding.

A secondary end seal 46 may be arranged on the primary end seal 44. The secondary end seal 46 may be suitably formed from a well-known self sealing, moldable, and flexible film (commercially available as Parafilm®). The secondary end seal 46 may be formed and attached to the primary end seal 44 by a well-known method, such as heat bonding or gluing. In some embodiments, a sealing wax may be used to facilitate bonding between the primary end seal 44 material and the film of the secondary end seal 46. In some embodiments, the secondary end seal 46 includes one or more dimples 50, each having a substantially parabolic shape. The properties of dimples 50 according to embodiments of the disclosure will be described in further detail below.

Figure 22:
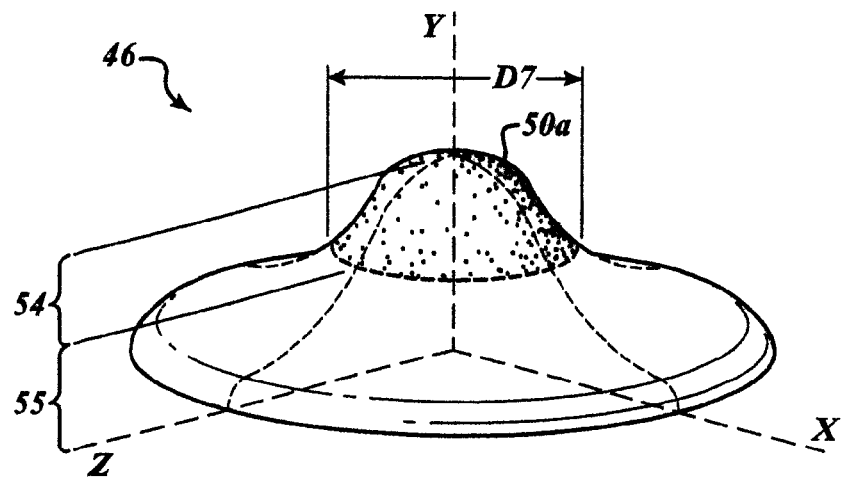
FIGS. 22 and 23 are perspective views of embodiments of end seal assemblies according to embodiments of the disclosure.
Figure 23:
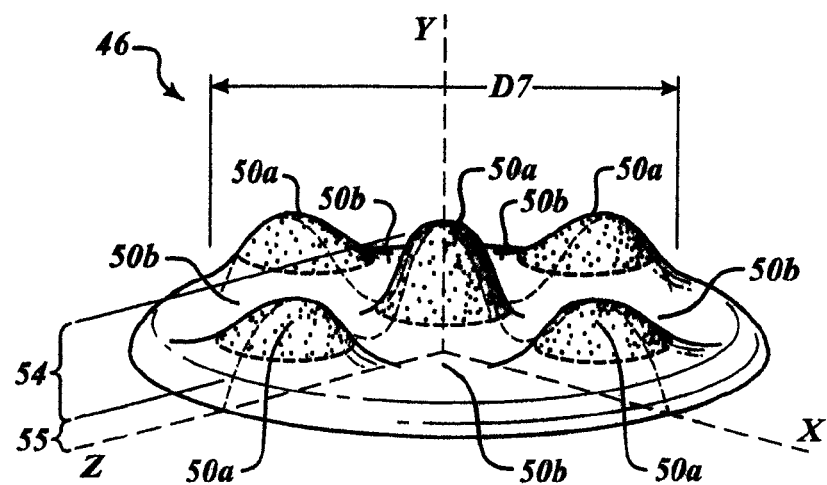

Referring to FIGS. 22 and 23, secondary end seals 46 according to embodiments of the disclosure are shown having outwardly extending dimples 50a and inwardly extending dimples 50b. Embodiments of secondary end seals 46 according to the disclosure may comprise a single dimple or more than one dimple. For example, as shown in FIG. 22, the secondary end seal 26 includes a single outwardly extending dimple 50a. In other embodiments, the secondary end seal 46 may comprise more than one dimple (e.g. FIG. 23). Some of the dimples may extend inwardly while others may extend outwardly.

Dimples 50 according to the disclosure may be formed by using a suitably shaped steel pin (or another equivalent device) to stretch the Parafilm®. Pins used according to methods in the disclosure may be parabolic, ellipsoid, hemispherical, or any other suitable shape known to a person of ordinary skill in the art. The stretching results in a subtle loss of breaking strength in the stretched areas of the secondary end seal 46. In some embodiments, the resulting loss in breaking strength may be anywhere from about 10% to about 30%. Accordingly, when the embryo emerges from the seed shell 12, it is exposed to a secondary end seal 46 having a non-uniform breaking strength across its surface.

Referring to FIGS. 22 and 23, the dimple or dimples 50 on the secondary end seal 46 define a pre-stressed area 54 that has a lower breaking strength than the rest of the dimple 50 (e.g., the non-pre-stressed area 55). In some embodiments, the pre-stressed area 54 has a pre-stressed diameter D7 that is at least as wide as the cavity diameter D5. In some embodiments, D7 may be about 50% to about 95% as wide as D5. In some cases, seal assemblies 16 having a pre-stressed area 54 that is almost as wide or significantly wider than the cavity diameter D5 may be particularly helpful in promoting germination. For example, D7 may be about 80% to about 300% as wide as D5.

Figure 21:
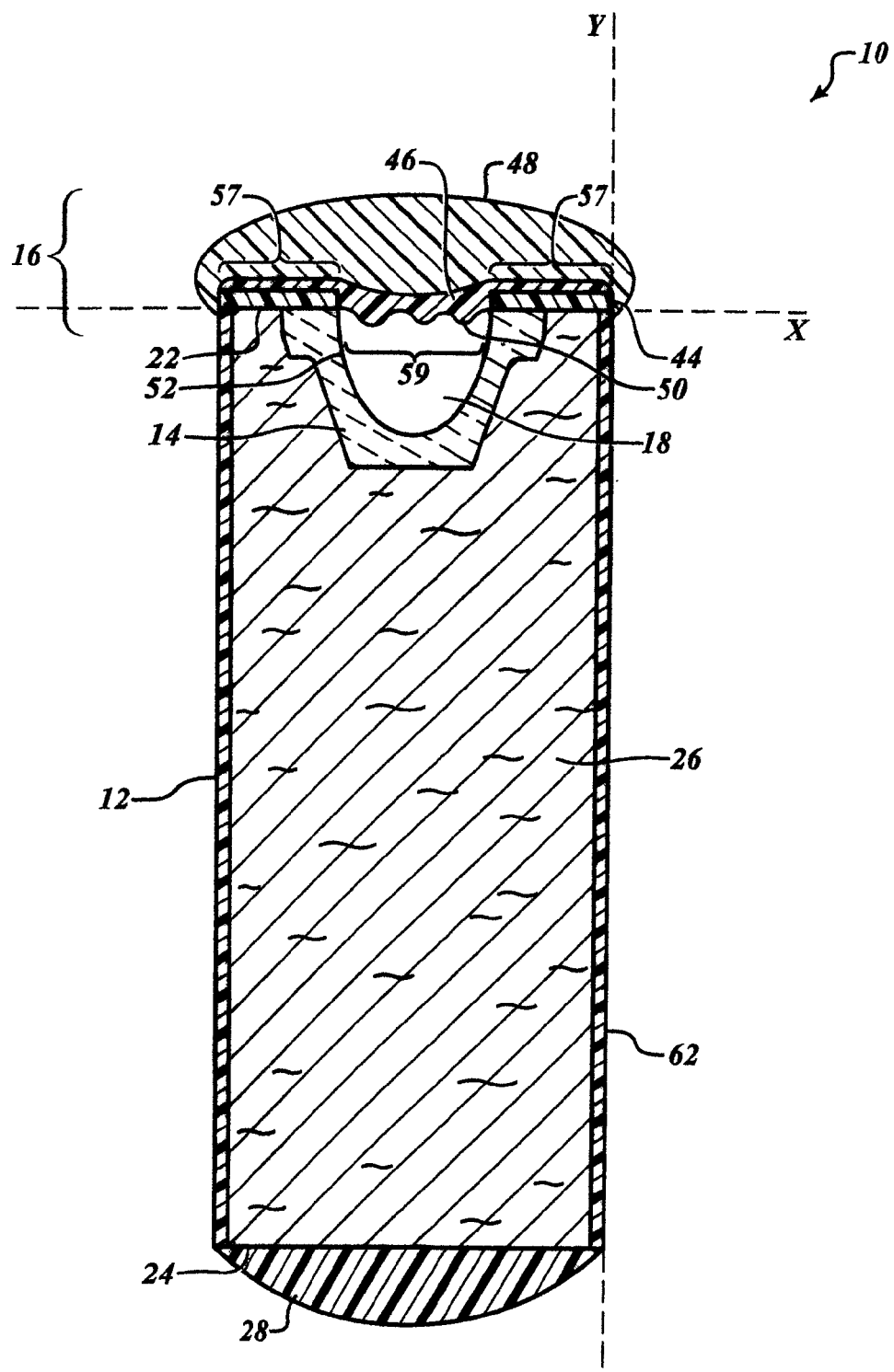

Referring back to FIGS. 16-21, secondary end seals 46 according to embodiments of the disclosure may include dimples 50 having various dimple depths L8 and dimple diameters D6. In some embodiments (e.g., FIG. 17) dimple diameters D8 can be about the same size as the seed shell diameter D1. In other embodiments, dimple diameters D8 are smaller. Dimple depths L8 may be as deep as 0.04 inches. Outwardly extending dimple depths L8 are measured according to the distance that the dimple 50 extends away from the closed end 24 of the seed shell 12. Inwardly extending dimple depths L8 are measured according to the distance that the dimple 50 extends towards the closed end 24 of the seed shell 12. Referring specifically to FIG. 21, in some embodiments, dimples 50 according to embodiments of the disclosure may extend past the primary end seal 44 towards the closed end 24 of the seed shell. In some cases, a first portion of the secondary end seal 46 is disposed on one side of the primary end seal 44 while a second portion of the secondary end seal 46 remains on the opposite side of the primary end seal 44.

A person of ordinary skill in the art will appreciate that a single secondary end seal 46 may have a single dimple 50 or more than one dimple 50. If the secondary end seal 46 has more than one dimple 50, the dimensions of each dimple 50 may be uniform or may vary substantially. Further, a single secondary end seal 46 may comprise both inwardly extending dimples 50a and outwardly extending dimples 50b.

In some embodiments, a tertiary end seal 48 may be arranged on the secondary end seal 46. The tertiary end seal 48 may be made from a material that degrades in structural integrity after a predetermined exposure to environmental conditions. The tertiary seal 48 also serves as an anti-microbial barrier to protect around the live end of the manufactured seed as the embryo germinates and emerges from within the seed shell 12. Suitable materials used to manufacture the tertiary seals 48 include water soluble materials, wax, environmentally degradable materials, and biodegradable materials.

Treated Seal Assemblies

Seal assemblies 16 may be treated with a substance to improve germination of embryos 20 within the seed shell 12. Paraffin oil has been found to be a suitable treatment due to its ability to soften portions of the sealing assembly 16. In some embodiments, the secondary end seal 46 is coated with a paraffin oil in a quantity sufficient to reduce the breaking strength of the secondary end seal 46. This amount may vary depending on whether the secondary end seal 46 has been pre-stressed according to some embodiments described above. In some embodiments, the secondary end seal is not pre-stressed and paraffin oil is applied. The surface of the secondary end seal 46 may be partially coated with paraffin oil or the entire surface of the secondary end seal 46 may be covered with the paraffin oil.

Varying amounts of paraffin oil may be used according to embodiments of the disclosure. Too little paraffin oil may be insufficient to reduce breaking strength and encourage germination. However, too much paraffin oil may cause root damage. In some embodiments, a suitable range of paraffin oil is approximately 0.5 mg to approximately 10.0 mg. In other embodiments, a suitable range of paraffin oil is approximately 3.0 mg to approximately 6.0 mg.

Different types of paraffin oils may be suitable for use with embodiments according to the disclosure. In a non-limiting example, suitable paraffin oils have a density of approximately 0.827 g/mL to approximately 0.890 g/mL at 20° C. In another non-limiting example, suitable paraffin oils have a dynamic viscosity approximately 110 mPas to approximately 230 mPas. Paraffin oils according to the disclosure may be in the form of viscous liquids or may include solids.

Embryo Orientation

Figure 24:
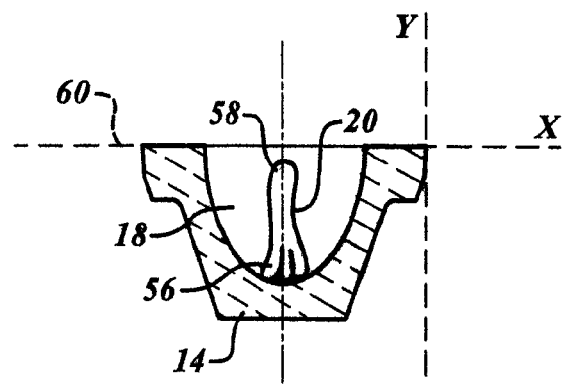
FIGS. 24-26 are side views of cavities having embryos disposed therein according to embodiments of the disclosure.
Figure 25:
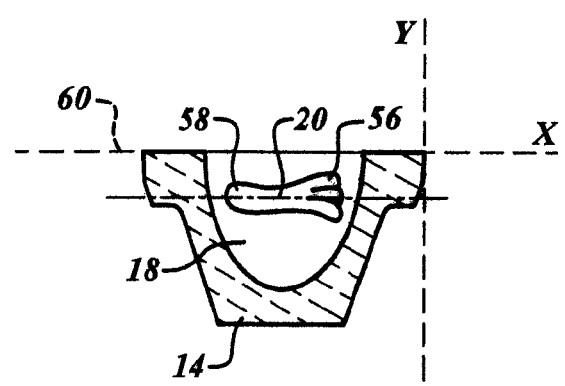
Figure 26:
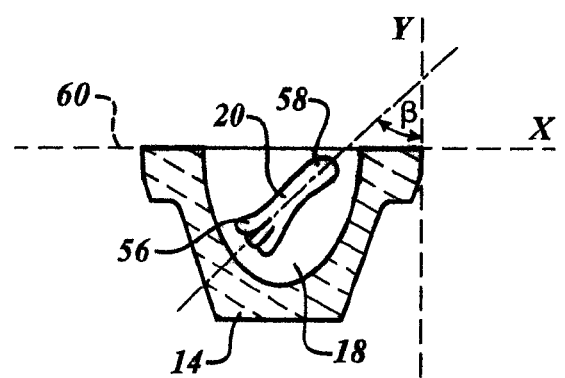

As described above, an embryo 20 may be disposed in the cavity 18 of manufactured seeds according to embodiments of the disclosure. FIGS. 24-26 illustrate different orientations of embryos in shoot restraints 14 having cavities 18 according to embodiments of the disclosure. Each embryo 20 includes a shoot end 56 and a root end 58. In some embodiments, the shoot end 56 may comprise one or more cotyledons if the type of embryo used in the manufactured seed has cotyledons. In some embodiments, cotyledons may be removed from the shoot end 56 of the embryo 20 prior to inserting the embryo 20 into the cavity 18.

Generally the embryo 20 is oriented shoot end 56 first. FIG. 24 shows an embodiment in which the embryo 20 is disposed in a perpendicular orientation with respect to a plane 60 in which the sealing assembly (not shown in the Figure) is arranged. FIG. 25 shows an embodiment in which the embryo 20 is disposed in a parallel orientation with respect to the plane 60. FIG. 26 shows an embodiment in which the embryo 20 is disposed in a skew or sloped orientation with respect to a plane 60. In FIG. 26, a slope angle $\beta$ is shown defined by the embryo 20 and the Y-axis or a sidewall 62 (see, e.g., FIGS. 1, 2, 6, and 7) of the seed shell 12. The slope angle $\beta$ may be less than 90 degrees. In some preferred embodiments, the slope angle $\beta$ is about 45 degrees to about 70 degrees.

Words in the above disclosure using the singular or plural number may also include the plural or singular number, respectively. For example, the term "dimple" could also apply to "dimples." Additionally, the words "herein," "above," "below" and words of similar import, when used in this application, shall refer to this application as a whole and not to any particular portions of this application.

From the foregoing, it will be appreciated that the specific embodiments of the disclosure have been described herein for purposes of illustration, but that various modifications may be made without deviating from the disclosure. For example, the dimensions described in this disclosure may be modified without changing the general sizing relationships between various components. Additionally, materials known to a person of ordinary skill in the art that are not explicitly listed may be used instead of the materials explicitly described.

Aspects of the disclosure described in the context of particular embodiments may be combined or eliminated in other embodiments. For example, features of manufactured seeds described as being useful for agricultural embryos may be combined with features of manufactured seeds described as being useful for tree embryos. Additionally, orientations of embryos shown with particular embodiments of shoot restraints may be used with other embodiments.

Further, while advantages associated with certain embodiments of the disclosure may have been described in the context of those embodiments, other embodiments may also exhibit such advantages, and not all embodiments need necessarily exhibit such advantages to fall within the scope of the disclosure. For example, manufactured seeds having only coated seal assemblies according to the disclosure may or may not have all of the advantages of manufactured seeds having parabolic shoot restraints, parabolic seal assemblies, and treated seal assemblies according to the disclosure. Accordingly, the invention is not limited except as by the appended claims.

EXAMPLES

The following examples will serve to illustrate aspects of the present disclosure. The examples are intended only as a means of illustration and should not be construed to limit the scope of the disclosure in any way. Those skilled in the art will recognize many variations that may be made without departing from the spirit of the disclosure. Certain terminology used in the disclosure are defined as follows:

"Grew between seal assembly" refers to an abnormal growth pattern characterized by an embryo that elongates to grow between the primary end seal and the secondary end seal in a manufactured seed.

"Grew through" refers to a germinant that emerges through a secondary end seal but part of the end seal is still attached to the hypocotoyl.

"Lateral root" means a secondary root or a root that has its origins from the primary root. The presence of a lateral root generally indicates health and vigor of the embryo.

"Normalcy" with respect to embryo germination denotes the presence of all plant parts (radicle, hypocotyls, cotyledon(s), epicotyls) and no abnormal growth at time of evaluation. Generally the radicle should be at least 3 mm long after at least 24 days germination to denote normalcy. A "normal germinant" has all of the plant parts described above, a radicle with a length greater than 3 mm after at least 24 days germination, and no visibly and immediately discernable abnormal growth patterns.

"Pretzeled hypocotyls" refers to a type of abnormal growth characterized by abnormally looped, twisted, and/or kinked hypocotyls. This type of abonormal growth is often associated with mechanical resistance to elongation during germination.

"Root end in air" refers to a type of abnormal growth characterized by an inverted orientation of the root end. This type of abnormal growth is thought occur when the geotropic sensing organ of the root is damaged or missing.

"Root in cavity" refers to a condition where the root end of the germinant fails to emerge from the seed or grows back into the cavity upon germination.

Generally, the types of abnormal growth observed in the Examples do not indefinitely indicate that there is a germination problem that will be fatal to the embryos. However, noting the quantity and quality of abnormal growth patterns is a reliable way to comparatively evaluate the various methods and means employed for making manufactured seeds. Fortunately, plant embryonic tissue is exquisitely sensitive to non-natural conditions and manifests that sensitivity in ways discernable to a trained observer.

Example 1

Breaking Strength of Conventionally Treated Seal Assemblies

In a first example, seal assemblies were treated with various conventional coatings and the resulting breaking strength were measured. For this experiment, manufactured seeds having conventional seal assemblies and conventional shoot restraints were provided. Secondary end seals were provided and treated with six different coatings (applied with a paintbrush) and tested 18 hours after application to determine breaking strength. The six different coatings were: (1) no coating; (2) petroleum jelly; (3) a mixture of petroleum jelly and triple antibiotic ointment; (4) silicone grease; (5) lanolin heated to 37° C.; and (6) lanolin heated to 50° C. Approximately 30 specimens of each type were tested.

Figure 27:
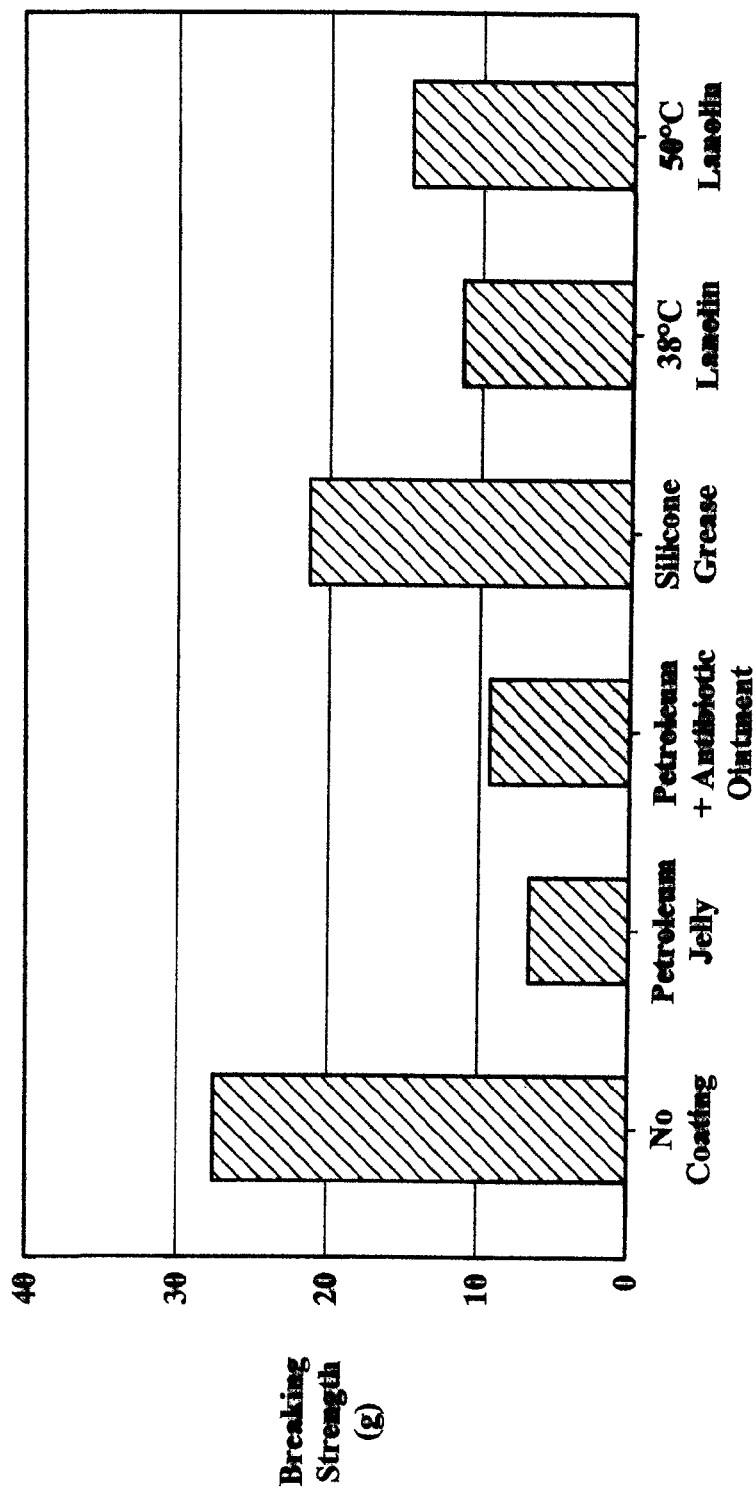
FIG. 27 is a bar chart showing breaking strength of seal assemblies treated with conventional coatings.

The secondary end seals were made from Parafilm® manufactured by American Can Company, Chicago, Ill. and supplied by VWR (catalog #52858-032). The end seals were each stretched to a diameter of about 0.10 inches prior to application of the coatings. The triple antibiotic ointment purchased over-the-counter from Rite Aid™ Pharmacies. The lanolin product number L-7387 purchased from Sigma Chemical Company. The silicone grease manufactured by Dow Corning, Compound 4 Electrical Insulating. FIG. 27 summarizes the results.

Example 2

Figure 28:
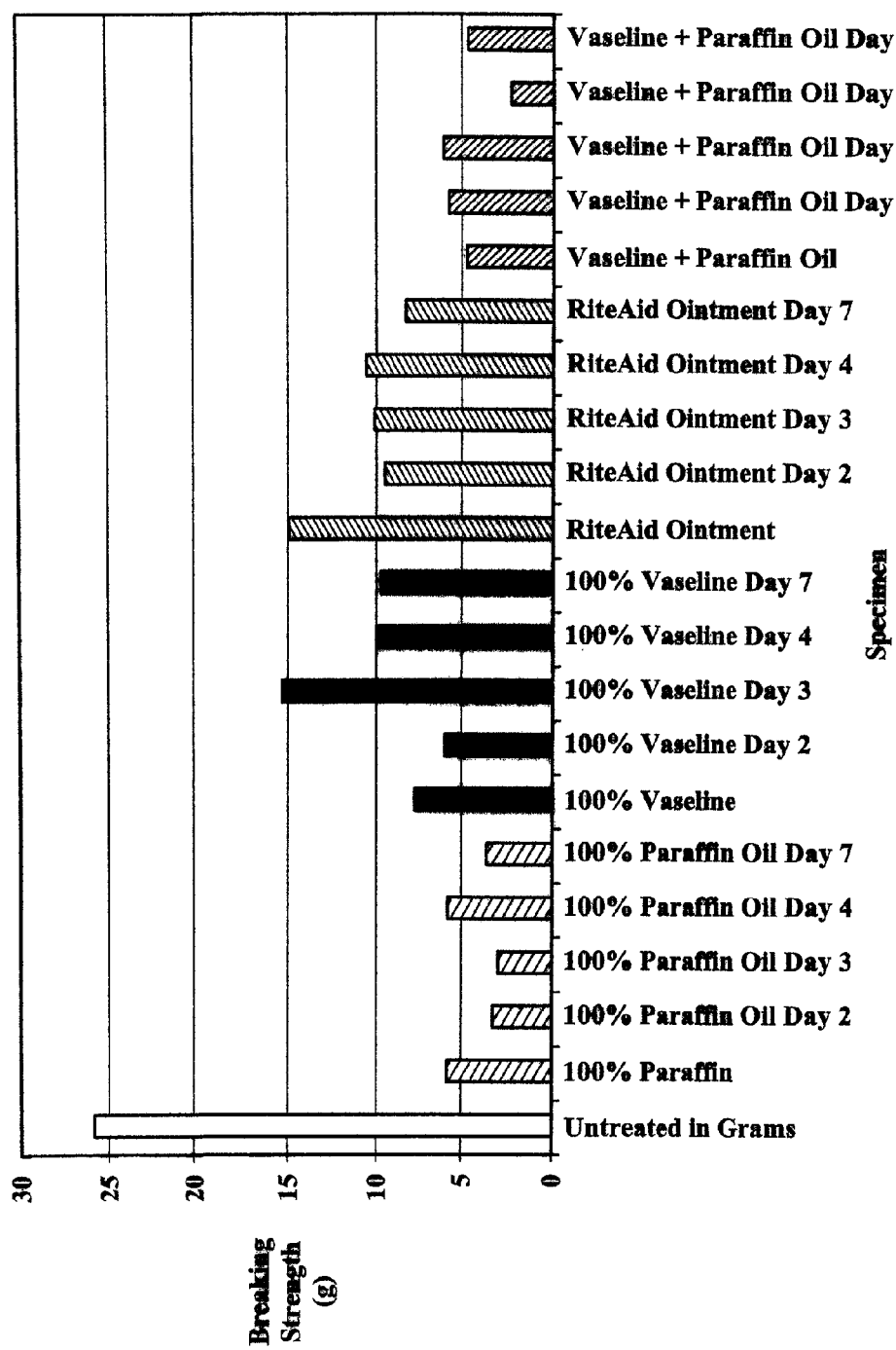
FIG. 28 is a bar chart showing breaking strength of seal assemblies treated according to embodiments of the disclosure and conventional seal assemblies.

Breaking Strength of Seal Assemblies Treated According to Embodiments of the Disclosure In a second example, the breaking strength of seal assemblies treated with paraffin oil according to embodiments of the disclosure were compared with conventional seal assemblies treated with conventional substances. For this experiment, secondary end seals were constructed in a manner similar to that described in Example 1. The secondary end seals were treated with paraffin oil, treated with Petroleum Jelly (Vaseline brand), treated with triple-antibiotic ointment, treated with a mixture of the previous components, or left untreated. Approximately 30 specimens of each type were tested. Some of the specimens were stored at room temperature while the treatment softened the end seal for up to seven days. FIG. 28 summarizes the resulting breaking strengths of each specimen.

Example 3

Impact of Paraffin Oil Level on Germination

In a third example, seal assemblies were treated with paraffin oil according to embodiments of the disclosure to evaluate the resulting impact on germination. For this experiment, manufactured seeds having conventional end seal assemblies and conventional shoot restraints were provided. The secondary end seals were treated with varying amounts of paraffin oil according to the treatment schedule in Table 2.

TABLE 2

Treatment Schedule for Example 3

| Treatment Number | Amount of Paraffin Oil | Number of Seeds |
| --- | --- | --- |
| T1 | 0.1 mg | 70 |
| T2 | 0.3 mg | 72 |
| T3 | 0.9 mg | 67 |
| T4 | 1.3 mg | 87 |

Figure 29:
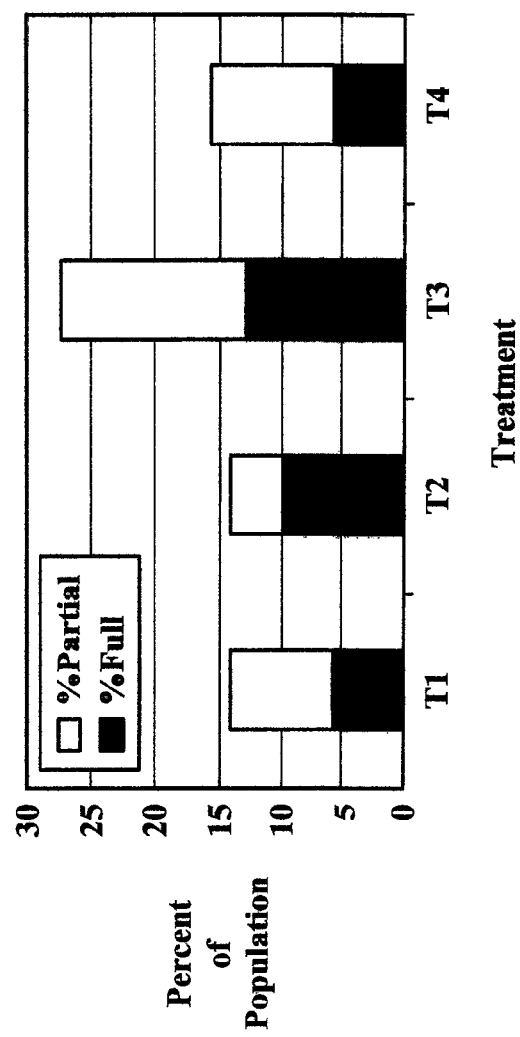
FIG. 29 is a bar chart showing percent population of partial germinants and full germinants in an Example.

After the paraffin oil was applied to the secondary end seal, the manufactured seeds were stored overnight in a refrigerator. A tertiary end seal was then attached to the secondary end seal, the seeds were sown in a non-sterile environment, and germination was observed for 43 days. FIG. 29 shows the percentage of the population in each treatment schedule that achieved full germination or partial germination.

This experiment provided evidence to support the hypotheses that too much paraffin oil on seal assemblies may inhibit germination. The T3 treatment (0.9 mg) exhibited the best performance. At day 43, the T4 treatment (1.3 mg) showed nearly equivalent performance to the T1 treatment (0.1 mg).

Example 4

Impact of Paraffin Oil Level and Pin Depth on Breaking Strength

In a fourth example, seal assemblies were treated with paraffin oil according to embodiments of the disclosure to evaluate the impact of increased oil levels on breaking strength. For this experiment, secondary end seals were constructed in a manner similar to that described in Examples 1 and 2. Prior to application of the paraffin oil, the secondary end seals were pre-stressed using pins to varying depths: 0.118 inches, 0.157 inches, and 0.192 inches. The secondary end seals were then treated with varying amounts of paraffin oil according to the treatment schedule in Table 3.

TABLE 3

Treatment Schedule for Example 4

| Treatment Number | Amount of Paraffin Oil | Pin Depth |
|---|---|---|
| T5 | 1.6 mg | .118 inches |
| T6 | 3.2 mg | .118 inches |
| T7 | 1.6 mg | .157 inches |
| T8 | 3.2 mg | .157 inches |
| T9 | 1.6 mg | .177 inches |
| T10 | 3.2 mg | .177 inches |
| T11 | 1.6 mg | .192 inches |
| T12 | 3.2 mg | .192 inches |

Figure 30:
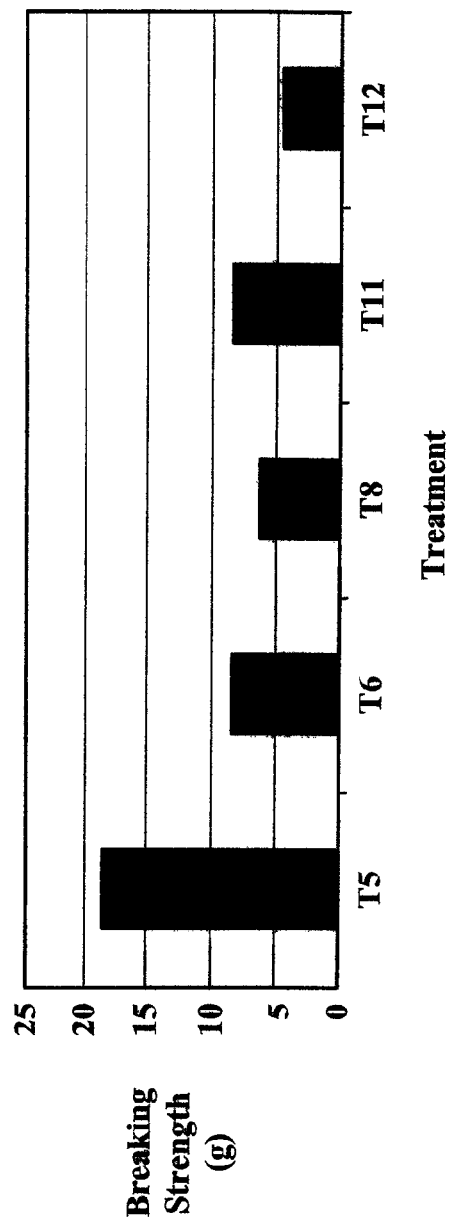
FIGS. 30 and 31 are bar charts showing breaking strength of seal assemblies treated according to embodiments of the disclosure.
Figure 31:
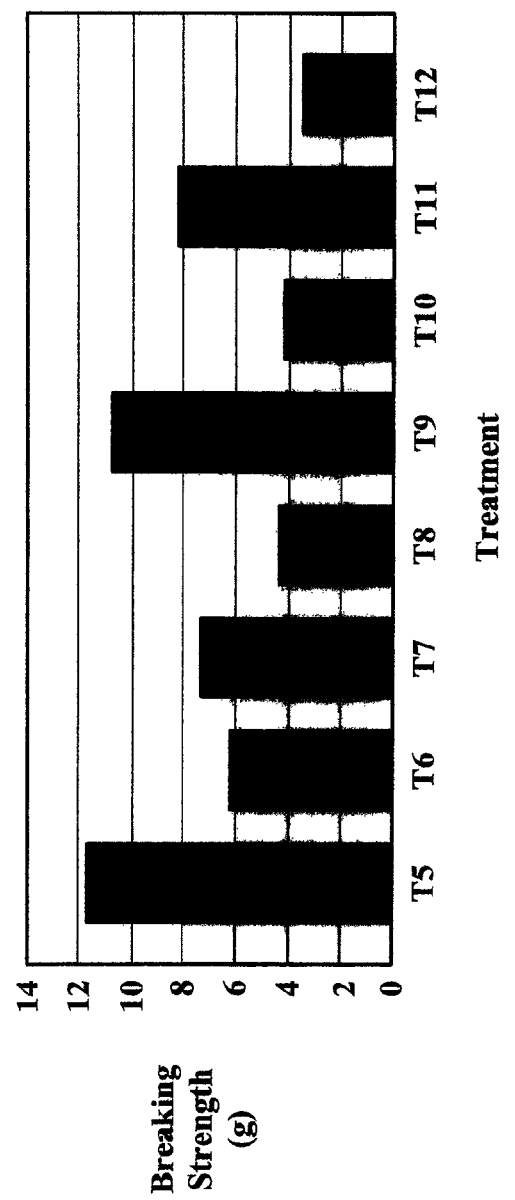

After the paraffin oil was applied to the secondary end seal, breaking strength was measured at 24 hours and 48 hours respectively. FIG. 30 shows representative results of the measurements at 24 hours. FIG. 31 presents the results of the measurements at 48 hours.

Example 5

Impact of Paraffin Oil Level on Breaking Strength, Germination, and Root Damage

In a fifth example, seal assemblies were treated with paraffin oil according to embodiments of the disclosure to evaluate the impact of increased oil levels on breaking strength, germination, and root damage. For this experiment, manufactured seeds having conventional seal assemblies and conventional shoot restraints were provided. Prior to application of the paraffin oil, the secondary end seals were pre-stressed using pins to a depth of 0.192 inches. The secondary end seals were then treated with varying amounts of paraffin oil according to the treatment schedule in Table 4.

TABLE 4

Treatment Schedule for Example 5

| Treatment Number | Amount of Paraffin Oil |
|---|---|
| T13 | 1.6 mg |
| T14 | 3.2 mg |
| T15 | 6.4 mg |

Approximately 100 specimens for each treatment type (T13, T14, and T15) were sown in a sterile environment and allowed to germinate for 32 days. During this time, various properties indicative of abnormal growth or healthy germination were observed and scored. The results are summarized in Tables 5-8 below.

TABLE 5

Average Root Length (scored at 32 days)

| | Radicle Length (mm) | Hypocotyls Length (mm) | Cotyledon Length (mm) | Epicotyls Length (mm) |
|---|---|---|---|---|
| T13 | 32.6 | 25.70 | 20.54 | 11.27 |
| T14 | 39.19 | 28.97 | 20.56 | 10.83 |
| T15 | 25.86 | 23.84 | 20.67 | 9.57 |

Table 5 shows that the average radicle length for the 3.2 mg oil treatment (T14 treatment) was 39 mm compared to 25 mm for the 6.4 mg oil treatment (T15 treatment). It seems that 3.2 mg oil treatment (T14 treatment) allowed good root growth where the 6.4 mg oil treatment (T15 treatment) may have been too much oil resulting in inhibited growth.

TABLE 6

Percent Above/Below Germination (scored at 32 days)

| | 1 Full Germ | 2 Partial Germ | 3 No Germ | 4 Root End in Air | 5 Lateral Root Presence |
|---|---|---|---|---|---|
| T13 | 38.68% | 38.05% | 19.23% | 4.02% | 52.51% |
| T14 | 42.39% | 42.39% | 13.17% | 2.02% | 58.43% |
| T15 | 28.63% | 44.92% | 21.34% | 5.09% | 44.12% |

Table 6 shows a grouping of the seeds in Example 5 according to five normalcy categories: (1) full germination; (2) partial germination; (3) no germination; (4) root end in air; and (5) lateral root presence. The results Table 6 show a trend similar to Table 5. The 3.2 mg oil treatment (T14 treatment) performed the best with 42% full germinants. Table 5 shows that while the 6.4 mg oil treatment (T15 treatment) had 28% full germinants, it also had 44% partial germinants.

TABLE 7

Percent Above/Below Germination (scored at 32 days)

| | 1 Normal | 2 Normal if Fully Extracted | 3 Not Normal | 4 Unchanged | 5 Root in Cavity |
|---|---|---|---|---|---|
| T13 | 61.66% | 6.10% | 21.90% | 7.25% | 3.07% |
| T14 | 67.61% | 4.06% | 21.33% | 4.97% | 2.00% |
| T15 | 54.12% | 5.12% | 27.62% | 7.06% | 6.06% |

Table 7 shows a grouping of the seeds in Example 5 the seeds according to five normalcy categories: (1) normal germinants; (2) would be normal if fully extracted from seed; (3) not normal; (4) unchanged (no visible elongation); and (5) root in cavity. Table 7 shows the same trend with the 3.2 mg oil treatment (T14 treatment) having the best percent of normalcy at 67%. The 6.4 mg oil treatment (T15 treatment) had only 54% normalcy which is still well below the 3.2 mg oil treatment (T14 treatment). Each treatment had at least 20% in the "not normal" category.

TABLE 8

Percent with Seal Assembly Problems (scored at 32 days)

| | 1<br>No<br>Problems | 2<br>Grew Through,<br>Stuck to Hypo | 3<br>Grew Between<br>Seal Assembly | 4<br>Pretzeled<br>Hypo |
|---|---|---|---|---|
| T13 | 59.03% | 14.83% | 2.91% | 5.11% |
| T14 | 57.55% | 20.22% | 2.00% | 4.00% |
| T15 | 48.88% | 17.44% | 5.11% | 5.11% |

Table 8 shows a grouping of the seeds in Example 5 according to four categories indicating observable problems with the end seal assembly: (1) no problems; (2) grew through lid, lid is stuck to hypocotyls; (3) grew between seal assembly; (and (4) pretzeled hypocotyls. The 1× oil treatment (T13 treatment) had the least amount of seal assembly problems with 59% in the "no problems category. The 3.2 mg oil treatment (T14 treatment) was close being with 57% without problems. Table 8 also shows that all treatments had problems with the hypocotyls getting caught on the seal assemblies on their way out of the seed.

Example 6

Breaking Strength of Conventional Seal Assemblies and Seal Assemblies According to Embodiments of the Disclosure In a sixth example seal assemblies were treated with paraffin oil according to embodiments of the disclosure and conventional treatment to evaluate the impact on breaking strength. For this experiment, secondary end seals were constructed in a manner similar to that described in Examples 1, 2, and 4. Seven different treatment configurations were applied to the secondary end seals as summarized in Table 9.

TABLE 9

Configurations for Example 6

| | Seal Assembly | Paraffin Oil Coating | Paraffin Oil Amount |
|---|---|---|---|
| T16 | Conventional (dome) | Untreated | N/A |
| T17 | Conventional (dome) | Treated | 1.6 mg |
| T18 | Parabolic dimple | Untreated | N/A |
| T19 | Parabolic dimple | Treated | 1.6 mg |
| T20 | Parabolic dimple | Treated | 3.2 mg |
| T21 | Parabolic dimple | Treated | 6.4 mg |
| T22 | Parabolic dimple | Treated | 8.0 mg |

Figure 32:
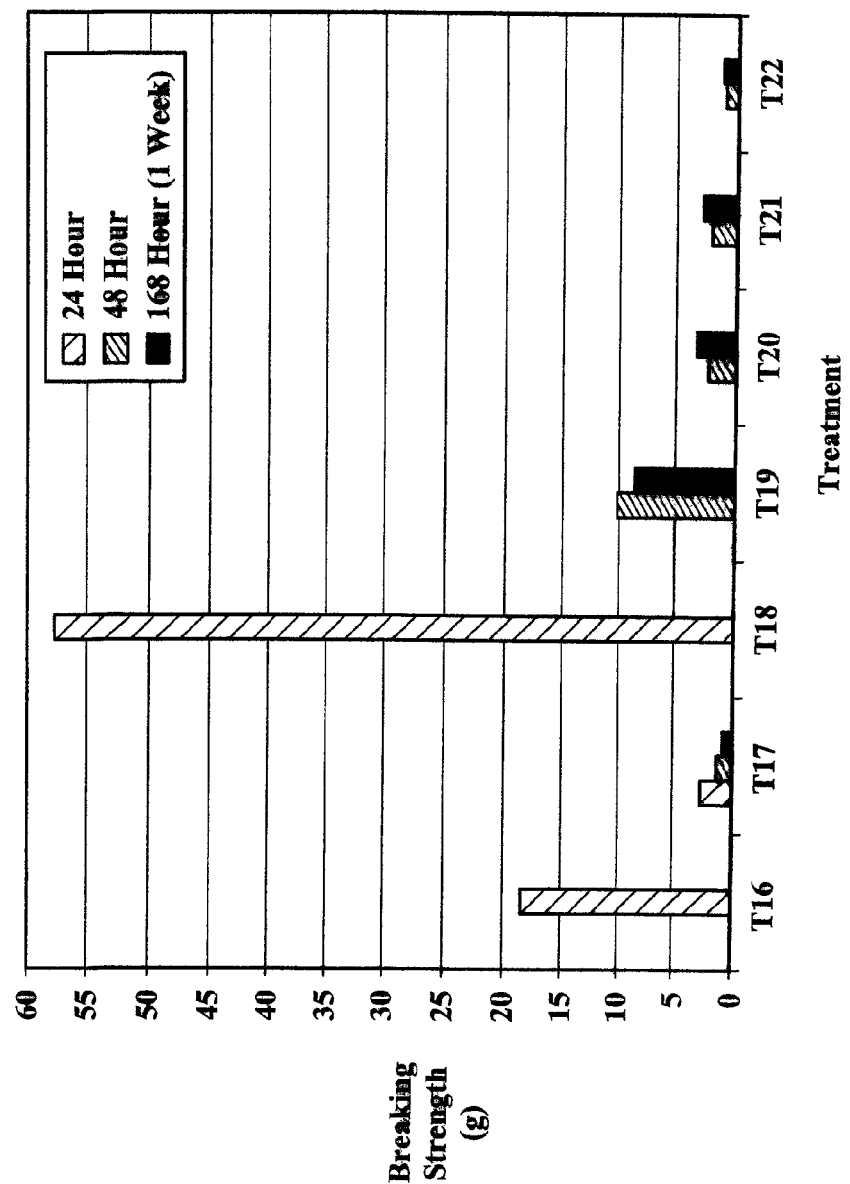
FIG. 32 is a bar chart showing breaking strength of seal assemblies according to embodiments of the disclosure and conventional seal assemblies.

Breaking strengths of the seal assemblies were measured at various times ranging from 24 hours to 2 weeks. The results are shown in FIG. 32.

Example 7

Germination of Manufactured Seeds According to Embodiments of the Disclosure

In a seventh example, germination of manufactured seeds having seal assemblies and parabolic cavities according to embodiments of the disclosure were compared to conventional manufactured seeds. All seal assemblies were coated with paraffin oil according to embodiments of the disclosure. For this experiment, four different configurations were tested as summarized in Table 10.

TABLE 10

Configurations for Example 7

| | Seal Assembly | Cavity | Paraffin Oil Coating |
|---|---|---|---|
| T23 | Parabolic dimple | Parabolic | 8.0 mg |
| T24 | Parabolic dimple | Conventional | 8.0 mg |
| T25 | Conventional | Conventional | 1.6 mg |

Figure 33:
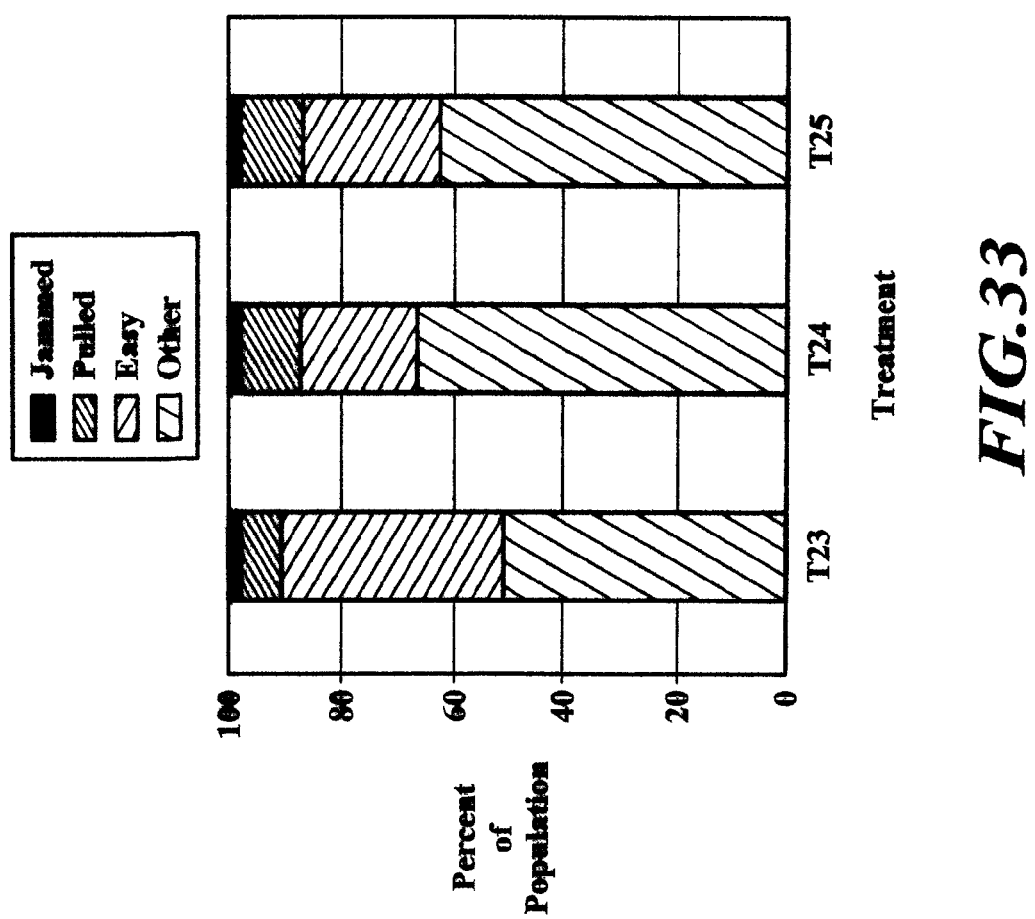
FIG. 33 is a bar chart showing effectiveness of cotyledon extraction for manufactured seeds according to embodiments of the disclosure and conventional seeds.
Figure 34:
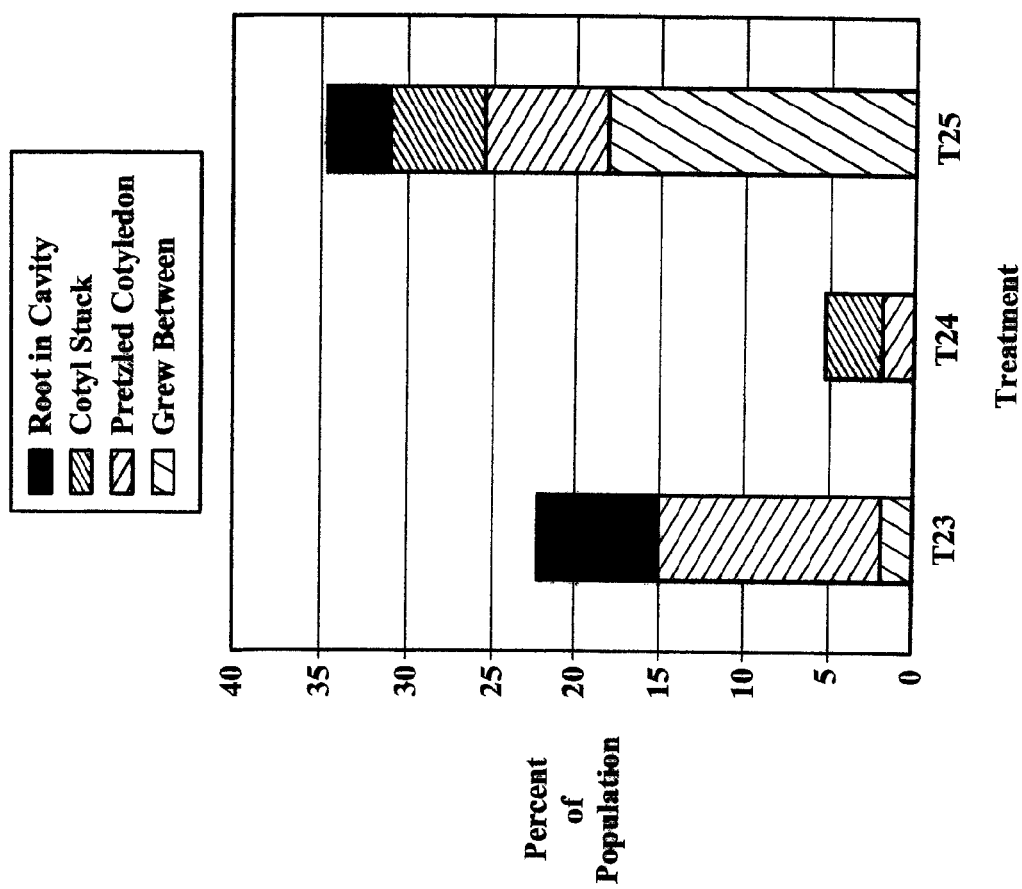
FIG. 34 is a bar chart showing germinants with extraction issues for manufactured seeds according to embodiments of the disclosure and conventional seeds.
Figure 35:
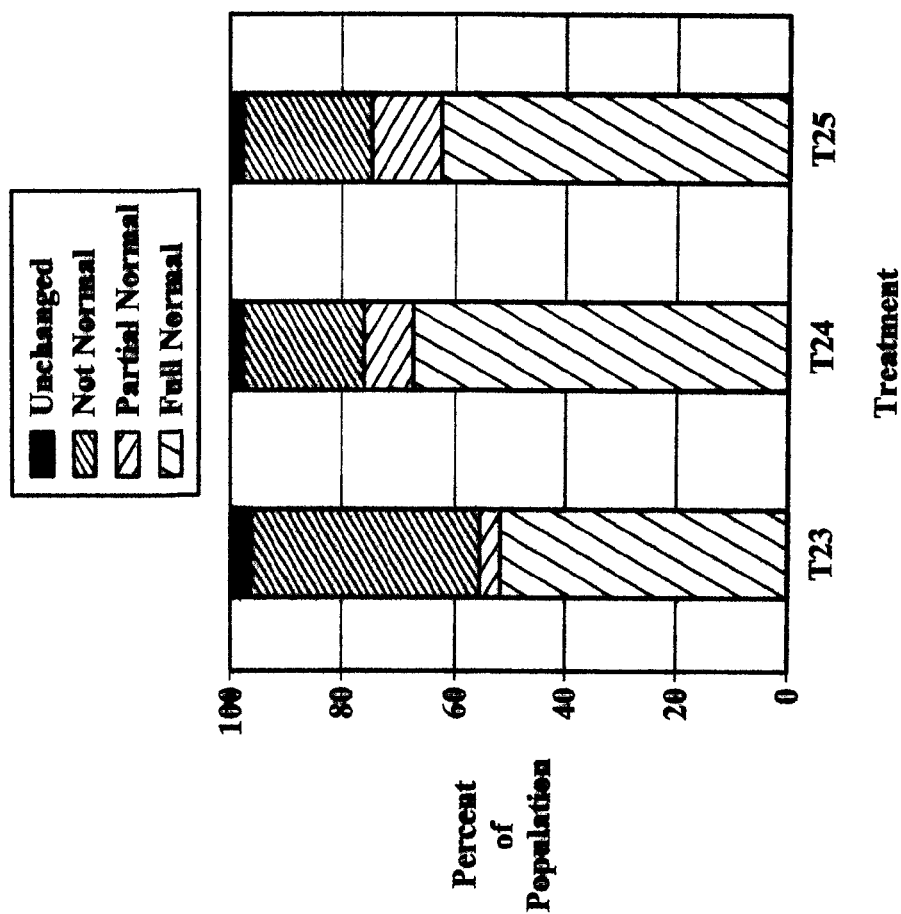
FIG. 35 is a bar chart showing normalcy for manufactured seeds according to embodiments of the disclosure and conventional seeds.

The seeds were sown in a sterile environment and allowed to germinate. Results are shown in FIGS. 33-35. FIG. 33 shows effectiveness of cotyledon extraction, FIG. 34 shows extraction hang-ups, and FIG. 35 shows normalcy. In this experiment, seal assemblies according to embodiments of the disclosure and conventional cavities significantly reduced lid hang-ups down to 6% and eliminated grow-betweens which have become a problem with other germination studies.

We claim:

1. A manufactured seed comprising:
    a seed shell comprising a structure having an open end and a closed end;
    a restraint disposed within the seed shell, the restraint comprising a cavity; and
    a seal assembly comprising a primary end seal and a secondary end seal, the secondary end seal being coated, at least partially, with a paraffin oil.

2. The manufactured seed of claim 1 wherein the paraffin oil is present in a quantity sufficient to reduce the secondary end seal's breaking strength.

3. The manufactured seed of claim 1 wherein the secondary end seal is coated completely in paraffin oil.

4. The manufactured seed of claim 2 wherein the quantity is approximately 0.5 mg to approximately 10.0 mg.

5. The manufactured seed of claim 2 wherein the quantity is approximately 3.0 mg to approximately 6.0 mg.

6. The manufactured seed of claim 1 wherein the paraffin oil has a density of approximately 0.827 g/mL to approximately 0.890 g/mL at 20° C.

7. The manufactured seed of claim 1 wherein the paraffin oil has dynamic viscosity approximately 110 mPas to approximately 230 mPas.

8. The manufactured seed of claim of claim 1 wherein the seal assembly further comprises a tertiary end seal.

9. The manufactured seed of claim 1, further comprising an embryo disposed within the cavity.

10. The manufactured seed of claim 1 wherein the secondary end seal comprises one or more parabolic dimples.

11. The manufactured seed of claim 1 wherein the one or more parabolic dimples are coated in paraffin oil.

12. The manufactured seed of claim 1 wherein the secondary end seal has a non-uniform breaking strength.

13. The manufactured seed of claim 1 wherein the cavity has a substantially parabolic shape.

14. The manufactured seed of claim 13, further comprising an embryo disposed within the cavity.

15. The manufactured seed of claim 14 wherein the embryo comprises a tree embryo.

16. The manufactured seed of claim 14 wherein the embryo comprises an agricultural crop embryo.

* * * * *